US011192013B2

(12) United States Patent
Dagenais

(10) Patent No.: US 11,192,013 B2
(45) Date of Patent: Dec. 7, 2021

(54) APPARATUS, SYSTEM AND METHOD FOR BODY TYPE SPECIFIC GOLF

(71) Applicant: Michel Dagenais, Gatineau (CA)

(72) Inventor: Michel Dagenais, Gatineau (CA)

( * ) Notice: Subject to any disclaimer, the term of this patent is extended or adjusted under 35 U.S.C. 154(b) by 0 days.

(21) Appl. No.: 16/821,196

(22) Filed: Mar. 17, 2020

(65) Prior Publication Data
US 2020/0215407 A1 Jul. 9, 2020

Related U.S. Application Data

(63) Continuation of application No. PCT/CA2018/051160, filed on Sep. 18, 2018.
(Continued)

(51) Int. Cl.
A63B 69/36 (2006.01)
A61B 5/107 (2006.01)
A63B 71/06 (2006.01)

(52) U.S. Cl.
CPC ........ A63B 69/3667 (2013.01); A61B 5/1072 (2013.01); A61B 5/1077 (2013.01);
(Continued)

(58) Field of Classification Search
CPC . A63B 69/3667; A63B 5/1072; A63B 5/1077; A63B 5/1079; A63B 71/0622;
(Continued)

(56) References Cited

U.S. PATENT DOCUMENTS 5,464,220 A * 11/1995 Hansen ............. A63B 69/3667
473/218
5,478,082 A * 12/1995 De Knight ......... A63B 69/3667
434/232
(Continued)

FOREIGN PATENT DOCUMENTS

CA 2627156 A1 * 11/2009 ............. A63F 13/02
GB 2398019 A * 8/2004 ......... A63B 69/3667
(Continued)

OTHER PUBLICATIONS

Notice of allowance in document issued by the OEE that indicates that claims 1-20 in the corresponding Canadian Application 3,063,935 were reviewed and considered to be allowable by the OEE, as well as copy of claims allowed.
(Continued)

Primary Examiner — Jeffrey S Vanderveen
(74) Attorney, Agent, or Firm — Andrews Robichaud PC

(57) ABSTRACT

Disclosed herein is automated guidance information regarding the stance or swing of golf player's as a function of each user's body type information, feet indicia, for indicating pre-determined positions on the ground to place the user's feet relative to one another; ball lines, and peg indicia, for guiding the movements of the user's body, or the user's golf club, relative to the peg indicia. Given the body type information of the user, body type specific information referencing a select body type specific feet indicia, a select body type specific ball line, or a select body type specific peg indicia is provided. Further disclosed are: (a) determining body type criteria information; (b) determining body type information using the body type criteria information; and (c) selecting from a plurality of body type specific information using the body type information.

19 Claims, 35 Drawing Sheets

Related U.S. Application Data

(60) Provisional application No. 62/560,320, filed on Sep. 19, 2017.

(52) U.S. Cl.
CPC ........ *A61B 5/1079* (2013.01); *A63B 71/0622* (2013.01); *A63B 2071/0625* (2013.01); *A63B 2071/0694* (2013.01); *A63B 2208/0204* (2013.01); *A63B 2220/05* (2013.01); *A63B 2225/50* (2013.01)

(58) Field of Classification Search
CPC ...... A63B 271/0625; A63B 2071/0694; A63B 2208/0204; A63B 2220/05; A63B 2225/50; A63B 5/1128
See application file for complete search history.

(56) References Cited

U.S. PATENT DOCUMENTS

| | | | | |
|---|---|---|---|---|
| 5,697,791 A | * | 12/1997 | Nashner | A63B 24/0003 434/247 |
| 6,106,408 A | * | 8/2000 | Roman | A63B 69/3667 473/217 |
| 6,174,270 B1 | | 1/2001 | Dagenais | |
| 7,527,562 B1 | * | 5/2009 | Mason | A63B 69/3667 473/218 |
| 9,211,439 B1 | * | 12/2015 | Pedenko | G16H 20/30 |
| 10,213,645 B1 | * | 2/2019 | Wu | A63B 71/0622 |
| 2010/0049468 A1 | * | 2/2010 | Papadourakis | A63B 69/3632 702/141 |
| 2016/0324445 A1 | * | 11/2016 | Kim | A61B 5/4528 |

FOREIGN PATENT DOCUMENTS

| | | | |
|---|---|---|---|
| GB | 2398019 A | | 8/2004 |
| JP | 2009273552 A | * | 11/2009 |
| JP | 2009273552 A | | 11/2009 |

OTHER PUBLICATIONS

Written Opinion of the International Searching Authority, International Application No. PCT/CA2018/051160, Canadian Intellectual Property Office, Dec. 18, 2018.

* cited by examiner

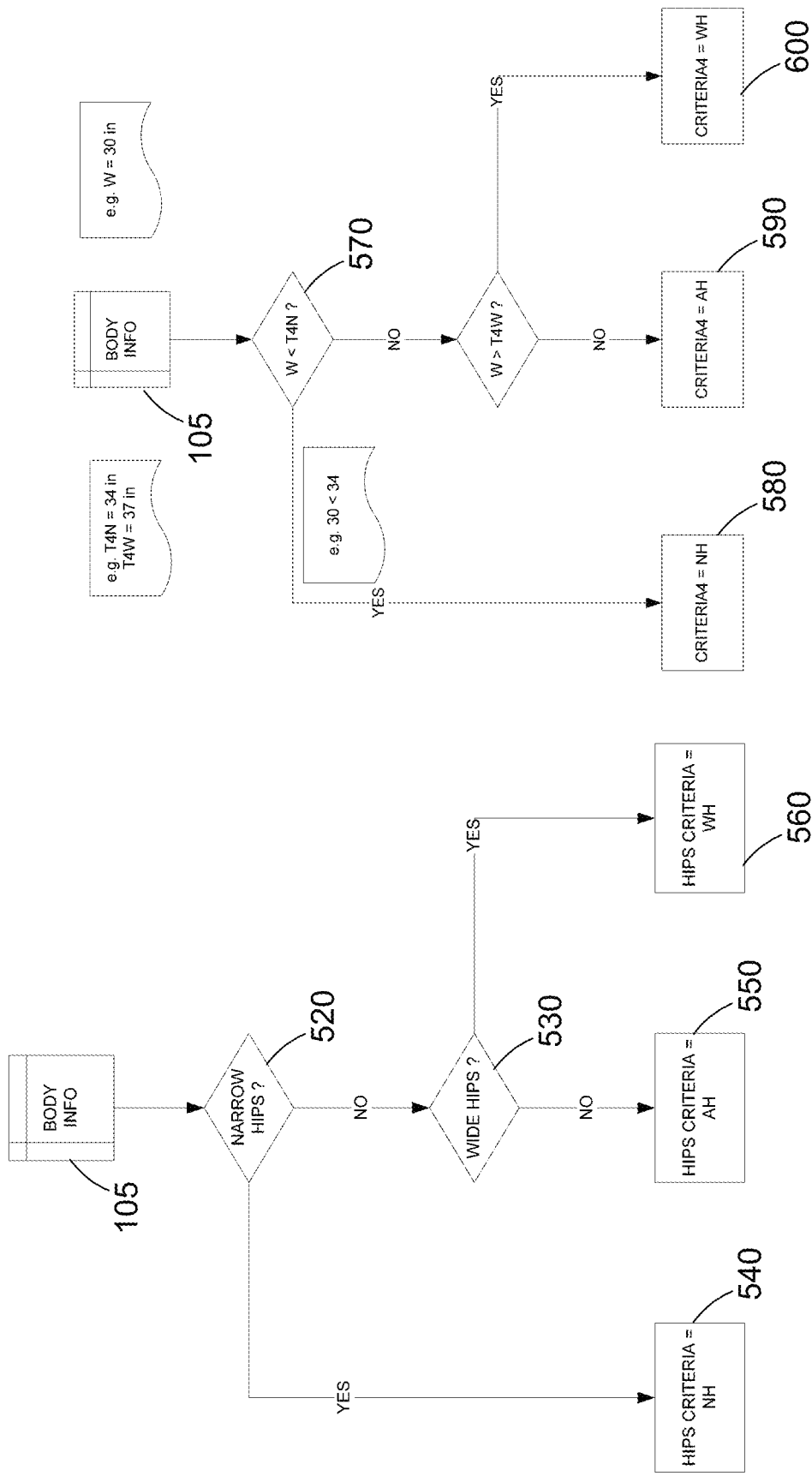

| BODY TYPE | CRITERIA 1 | CRITERIA 2 | CRITERIA 3 | CRITERIA 4 | CRITERIA 5 | INFORMATION |
|---|---|---|---|---|---|---|
| 1 | SA | SS02 | SP02 | NH | NS | INFORMATION 1 |
| 2 | SA | SS02 | SP02 | NH | AS | INFORMATION 2 |
| 3 | SA | SS02 | SP02 | NH | WS | INFORMATION 3 |
| 4 | SA | SS02 | SP02 | AH | NS | INFORMATION 4 |
| 5 | SA | SS02 | SP02 | AH | AS | INFORMATION 5 |
| 6 | SA | SS02 | SP02 | AH | WS | INFORMATION 6 |
| 7 | SA | SS02 | SP02 | WH | NS | INFORMATION 7 |
| 8 | SA | SS02 | SP02 | WH | AS | INFORMATION 8 |
| 9 | SA | SS02 | SP02 | WH | WS | INFORMATION 9 |
| 10 | SA | SS02 | SP24 | NH | NS | INFORMATION 10 |
| 11 | SA | SS02 | SP24 | NH | AS | INFORMATION 11 |
| 12 | SA | SS02 | SP24 | NH | WS | INFORMATION 12 |
| 13 | SA | SS02 | SP24 | AH | NS | INFORMATION 13 |
| 14 | SA | SS02 | SP24 | AH | AS | INFORMATION 14 |
| 15 | SA | SS02 | SP24 | AH | WS | INFORMATION 15 |
| 16 | SA | SS02 | SP24 | WH | NS | INFORMATION 16 |
| 17 | SA | SS02 | SP24 | WH | AS | INFORMATION 17 |
| 18 | SA | SS02 | SP24 | WH | WS | INFORMATION 18 |
| 19 | SA | SS24 | SP02 | NH | NS | INFORMATION 19 |
| 20 | SA | SS24 | SP02 | NH | AS | INFORMATION 20 |
| 21 | SA | SS24 | SP02 | NH | WS | INFORMATION 21 |
| 22 | SA | SS24 | SP02 | AH | NS | INFORMATION 22 |
| 23 | SA | SS24 | SP02 | AH | AS | INFORMATION 23 |
| 24 | SA | SS24 | SP02 | AH | WS | INFORMATION 24 |
| 25 | SA | SS24 | SP02 | WH | NS | INFORMATION 25 |
| 26 | SA | SS24 | SP02 | WH | AS | INFORMATION 26 |
| 27 | SA | SS24 | SP02 | WH | WS | INFORMATION 27 |
| 28 | SA | SS24 | SP24 | NH | NS | INFORMATION 28 |
| 29 | SA | SS24 | SP24 | NH | AS | INFORMATION 29 |
| 30 | SA | SS24 | SP24 | NH | WS | INFORMATION 30 |
| 31 | SA | SS24 | SP24 | AH | NS | INFORMATION 31 |
| 32 | SA | SS24 | SP24 | AH | AS | INFORMATION 32 |
| 33 | SA | SS24 | SP24 | AH | WS | INFORMATION 33 |
| 34 | SA | SS24 | SP24 | WH | NS | INFORMATION 34 |
| 35 | SA | SS24 | SP24 | WH | AS | INFORMATION 35 |
| 36 | SA | SS24 | SP24 | WH | WS | INFORMATION 36 |

FIG. 17

| BODY TYPE | CRITERIA 1 | CRITERIA 2 | CRITERIA 3 | CRITERIA 4 | CRITERIA 5 | INFORMATION |
|---|---|---|---|---|---|---|
| 37 | AA | SS02 | SP02 | NH | NS | INFORMATION 37 |
| 38 | AA | SS02 | SP02 | NH | AS | INFORMATION 38 |
| 39 | AA | SS02 | SP02 | NH | WS | INFORMATION 39 |
| 40 | AA | SS02 | SP02 | AH | NS | INFORMATION 40 |
| 41 | AA | SS02 | SP02 | AH | AS | INFORMATION 41 |
| 42 | AA | SS02 | SP02 | AH | WS | INFORMATION 42 |
| 43 | AA | SS02 | SP02 | WH | NS | INFORMATION 43 |
| 44 | AA | SS02 | SP02 | WH | AS | INFORMATION 44 |
| 45 | AA | SS02 | SP02 | WH | WS | INFORMATION 45 |
| 46 | AA | SS02 | SP24 | NH | NS | INFORMATION 46 |
| 47 | AA | SS02 | SP24 | NH | AS | INFORMATION 47 |
| 48 | AA | SS02 | SP24 | NH | WS | INFORMATION 48 |
| 49 | AA | SS02 | SP24 | AH | NS | INFORMATION 49 |
| 50 | AA | SS02 | SP24 | AH | AS | INFORMATION 50 |
| 51 | AA | SS02 | SP24 | AH | WS | INFORMATION 51 |
| 52 | AA | SS02 | SP24 | WH | NS | INFORMATION 52 |
| 53 | AA | SS02 | SP24 | WH | AS | INFORMATION 53 |
| 54 | AA | SS02 | SP24 | WH | WS | INFORMATION 54 |
| 55 | AA | SS24 | SP02 | NH | NS | INFORMATION 55 |
| 56 | AA | SS24 | SP02 | NH | AS | INFORMATION 56 |
| 57 | AA | SS24 | SP02 | NH | WS | INFORMATION 57 |
| 58 | AA | SS24 | SP02 | AH | NS | INFORMATION 58 |
| 59 | AA | SS24 | SP02 | AH | AS | INFORMATION 59 |
| 60 | AA | SS24 | SP02 | AH | WS | INFORMATION 60 |
| 61 | AA | SS24 | SP02 | WH | NS | INFORMATION 61 |
| 62 | AA | SS24 | SP02 | WH | AS | INFORMATION 62 |
| 63 | AA | SS24 | SP02 | WH | WS | INFORMATION 63 |
| 64 | AA | SS24 | SP24 | NH | NS | INFORMATION 64 |
| 65 | AA | SS24 | SP24 | NH | AS | INFORMATION 65 |
| 66 | AA | SS24 | SP24 | NH | WS | INFORMATION 66 |
| 67 | AA | SS24 | SP24 | AH | NS | INFORMATION 67 |
| 68 | AA | SS24 | SP24 | AH | AS | INFORMATION 68 |
| 69 | AA | SS24 | SP24 | AH | WS | INFORMATION 69 |
| 70 | AA | SS24 | SP24 | WH | NS | INFORMATION 70 |
| 71 | AA | SS24 | SP24 | WH | AS | INFORMATION 71 |
| 72 | AA | SS24 | SP24 | WH | WS | INFORMATION 72 |

FIG. 18

| BODY TYPE | CRITERIA 1 | CRITERIA 2 | CRITERIA 3 | CRITERIA 4 | CRITERIA 5 | INFORMATION |
|---|---|---|---|---|---|---|
| 73 | LA | SS02 | SP02 | NH | NS | INFORMATION 73 |
| 74 | LA | SS02 | SP02 | NH | AS | INFORMATION 74 |
| 75 | LA | SS02 | SP02 | NH | WS | INFORMATION 75 |
| 76 | LA | SS02 | SP02 | AH | NS | INFORMATION 76 |
| 77 | LA | SS02 | SP02 | AH | AS | INFORMATION 77 |
| 78 | LA | SS02 | SP02 | AH | WS | INFORMATION 78 |
| 79 | LA | SS02 | SP02 | WH | NS | INFORMATION 79 |
| 80 | LA | SS02 | SP02 | WH | AS | INFORMATION 80 |
| 81 | LA | SS02 | SP02 | WH | WS | INFORMATION 81 |
| 82 | LA | SS02 | SP24 | NH | NS | INFORMATION 82 |
| 83 | LA | SS02 | SP24 | NH | AS | INFORMATION 83 |
| 84 | LA | SS02 | SP24 | NH | WS | INFORMATION 84 |
| 85 | LA | SS02 | SP24 | AH | NS | INFORMATION 85 |
| 86 | LA | SS02 | SP24 | AH | AS | INFORMATION 86 |
| 87 | LA | SS02 | SP24 | AH | WS | INFORMATION 87 |
| 88 | LA | SS02 | SP24 | WH | NS | INFORMATION 88 |
| 89 | LA | SS02 | SP24 | WH | AS | INFORMATION 89 |
| 90 | LA | SS02 | SP24 | WH | WS | INFORMATION 90 |
| 91 | LA | SS24 | SP02 | NH | NS | INFORMATION 91 |
| 92 | LA | SS24 | SP02 | NH | AS | INFORMATION 92 |
| 93 | LA | SS24 | SP02 | NH | WS | INFORMATION 93 |
| 94 | LA | SS24 | SP02 | AH | NS | INFORMATION 94 |
| 95 | LA | SS24 | SP02 | AH | AS | INFORMATION 95 |
| 96 | LA | SS24 | SP02 | AH | WS | INFORMATION 96 |
| 97 | LA | SS24 | SP02 | WH | NS | INFORMATION 97 |
| 98 | LA | SS24 | SP02 | WH | AS | INFORMATION 98 |
| 99 | LA | SS24 | SP02 | WH | WS | INFORMATION 99 |
| 100 | LA | SS24 | SP24 | NH | NS | INFORMATION 100 |
| 101 | LA | SS24 | SP24 | NH | AS | INFORMATION 101 |
| 102 | LA | SS24 | SP24 | NH | WS | INFORMATION 102 |
| 103 | LA | SS24 | SP24 | AH | NS | INFORMATION 103 |
| 104 | LA | SS24 | SP24 | AH | AS | INFORMATION 104 |
| 105 | LA | SS24 | SP24 | AH | WS | INFORMATION 105 |
| 106 | LA | SS24 | SP24 | WH | NS | INFORMATION 106 |
| 107 | LA | SS24 | SP24 | WH | AS | INFORMATION 107 |
| 108 | LA | SS24 | SP24 | WH | WS | INFORMATION 108 |

FIG. 19

INFO #  CRITERIA 1
        CRITERIA 2
        CRITERIA 3          N VIDEOS
        CRITERIA 4          EXPECTED
        CRITERIA 5

BASIC SET UP GUIDANCE
        G1    GUIDANCE 1
        G2    GUIDANCE 2
        G3    GUIDANCE 3

BASICS GUIDANCE

Takeaway / backswing /impact GUIDANCE
        G4    GUIDANCE 4
        G5    GUIDANCE 5
        G6    GUIDANCE 6
        G7    GUIDANCE 7
        G8    GUIDANCE 8

Finish GUIDANCE
        G9    GUIDANCE 9
        G10   GUIDANCE 10
        G11   GUIDANCE 11

Body Type Specific GUIDANCE
        G12   GUIDANCE 12
        G13   GUIDANCE 13
        G14   GUIDANCE 14
        G25   GUIDANCE 15
        G16   GUIDANCE 16
        G17   GUIDANCE 17
        G18   GUIDANCE 18
        G19   GUIDANCE 19
        G20   GUIDANCE 20
        G21   GUIDANCE 21
        G22   GUIDANCE 22
        G23   GUIDANCE 23
        G24   GUIDANCE 24

FIG. 20

12  Short arms
    Slant 02
    Projection 24          24 videos
    Narrow hips            expect low ball flight
    Wide shoulders BASIC SET UP SHORT ARMS
    1    Set up right foot wider than left foot D and L
    2    Butt of the club over 16 at address
    3    Crotch over 16 at address

BASICS 1 PROJECTED

Takeaway / backswing /impact
    4    right knee stable on backswing / short peg on 2
    5    Takeaway long peg on 1
    6    buttocks over 13 at top of swing
    7    right knee at 5 at impact
    8    buttocks over 13 at impact Finish
    9    Finish belt buckle facing 15
    10   finish right knee over 11
    35   Finish hands over 14

Body Type Specific
    12   Left shoulder over 5 in takeaway
    13   Left shoulder to 6 top of the swing
    14   Hands to 7 top of the swing
    29   Backswing left knee goes to 5 by lifting left heel off the ground
    52   From top of the swing turn the hands so the club head goes to 14
    17   Left knee buckles to 10 in early part of transition while knee remains bent
    18   Right knee stays at 2 in transition while still bent and much of the weight stays on right leg during transition
    30   Keep buttocks over 13 in transition as sit on the heels
    20   Butt of club points to 3 half way in downswing
    50   Impact hands go over 12 while left leg straightens and hips turn around the left leg
    22   Keep head over 6 at impact
    24   Keep left shoulder over 12 at impact - do not go past 12 with left shoulder
    23   Post impact front edge of the grip goes over 17

What is your height in inches ?

What is your hip width in inches

What is your shoulder slant in inches ?

What is your shoulder width in inches ?

What is your shoulder projection in inches ?

What is your waist size in inches ?

What is your foot size in inches ?

CLICK TO CONTINUE

Upload your photos here.

Facing the camera:
[UPLOAD FILE]

Golf stance:
[UPLOAD FILE]

What is your height in inches ?
[        ]

What is your waist size in inches ?
[        ]

What is your foot size in inches ?
[        ]

( CLICK TO CONTINUE )

APPARATUS, SYSTEM AND METHOD FOR BODY TYPE SPECIFIC GOLF

CROSS-REFERENCE TO RELATED APPLICATIONS

This application is related to and claims priority from U.S. Provisional Applications 62/560,320 entitled "APPARATUS, SYSTEM AND METHOD FOR BODY TYPE SPECIFIC GOLF", by Michael M. Dagenais, filed 19 Sep. 2017. This application is related to and claims priority from, Patent Cooperation Treaty International Application No. PCT/CA2018/051160 entitled "APPARATUS, SYSTEM AND METHOD FOR BODY TYPE SPECIFIC GOLF", by Michael M. Dagenais, filed 18 Sep. 2018.

TECHNICAL FIELD

This application relates to golf in general, and to an apparatus, system and method for body type specific golf, in particular.

SUMMARY

According to one aspect of the present techniques, there is provided an apparatus, system and method for body type specific golf.

The apparatus is for providing guidance information regarding the stance or swing of golf player's as a function of each user's body type information. In some embodiments, the apparatus includes: (a) a plurality of feet indicia, for indicating pre-determined positions on the ground to place the user's feet relative to one another; (b) a plurality of ball lines, for indicating pre-determined positions on the ground relative to the feet indicia, to place a golf ball relative to the ball lines; and (c) a plurality of peg indicia, for indicating pre-determined positions on the ground relative to the feet indicia, for guiding the movements of the user's body, or the user's golf club, relative to the peg indicia. The pre-determined positions on the ground of the plurality of feet indicia, plurality of ball lines, and plurality of peg indicia account for a plurality of body types of golf player's, such that, given the body type information of the user, body type specific information referencing a select body type specific feet indicia, a select body type specific ball line, or a select body type specific peg indicia is provided, the body type specific information including body type specific guidance to guide the stance or swing of the user as a function of the user's body type information.

In some embodiments, the apparatus includes: (a) a body type criteria determination component to determine body type criteria information; (b) a body type determination component to determine body type information using the body type criteria information; and (c) a body type specific information selection component to select from a plurality of body type specific information using the body type information.

In some embodiments, the method includes the acts of: (a) determining body type criteria information; (b) determining body type information using the body type criteria information; and (c) selecting from a plurality of body type specific information using the body type information.

These and other aspects and features of the present techniques will become apparent to those ordinarily skilled in the art upon review of the following description of specific embodiments of an apparatus, system and method for body type specific golf in conjunction with the accompanying drawing figures.

BRIEF DESCRIPTION OF THE DRAWINGS

Embodiments of the present techniques will now be described, by way of example only, with reference to the accompanying drawing figures, wherein:

FIG. 13 is an illustration of a flowchart of exemplary steps to determine hip width criteria using hip body information;

FIG. 14 is an illustration of a flowchart of exemplary steps to determine the fourth criteria of FIG. 13 using the exemplary hip body information of FIG. 5;

FIG. 17 is an illustration of an exemplary beginning third of an exemplary body type specific information lookup table;

FIG. 18 is an illustration of an exemplary middle third of an exemplary body type specific information lookup table;

FIG. 19 is an illustration of an exemplary ending third of an exemplary body type specific information lookup table;

FIG. 20 is an exemplary information record structure including body type specific information structure;

FIG. 21 is an exemplary information record data including body type specific information data;

FIG. 22 is an illustration an exemplary user interface for determining exemplary body information without the need for photographs;

FIG. 23 is an illustration an exemplary user interface for determining exemplary body information using photographs;

Like reference numerals are used in different figures to denote similar elements.

DETAILED DESCRIPTION OF THE DRAWINGS

Figure 1:
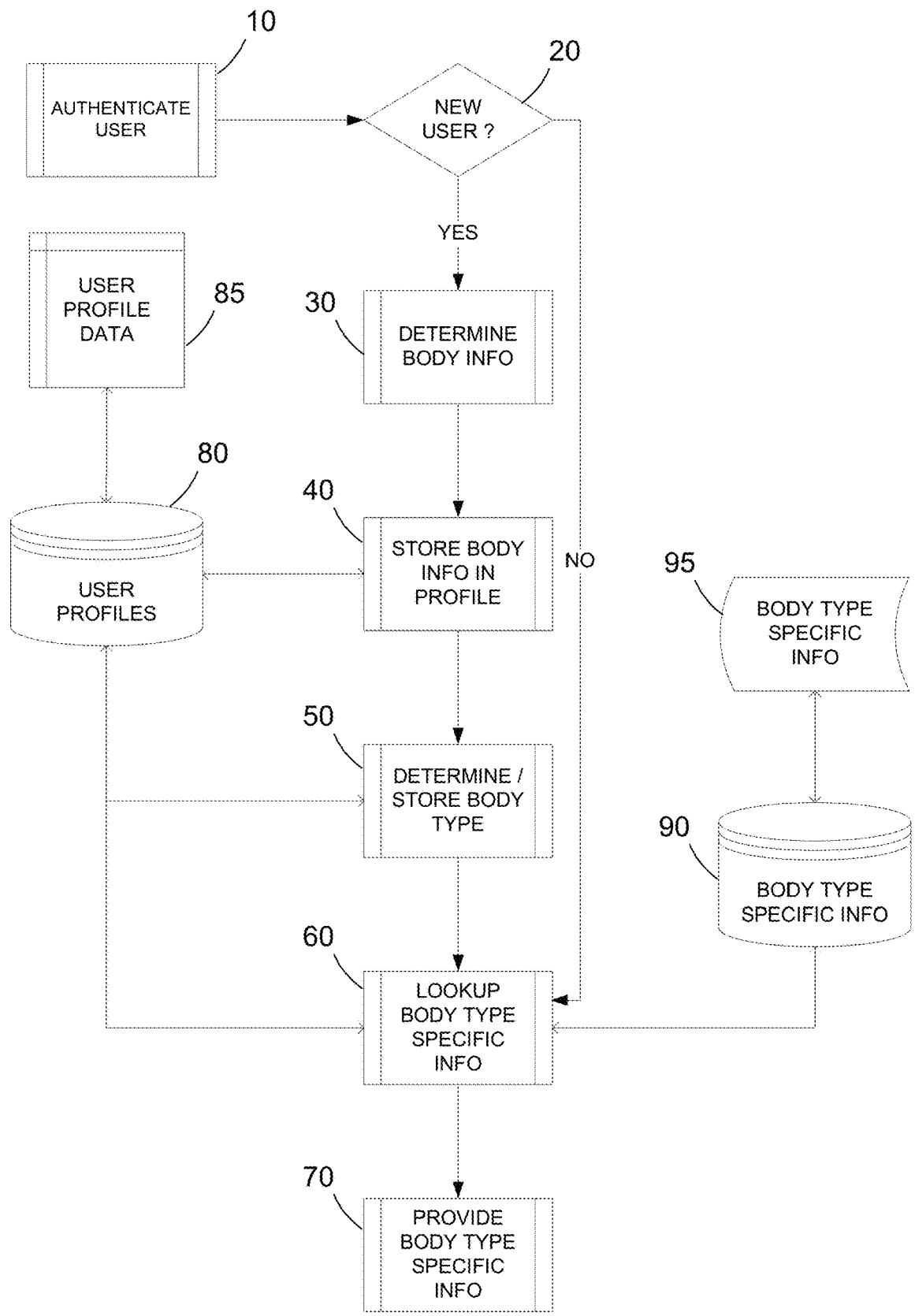
FIG. 1 is a flowchart of an exemplary body type specific information management method.

Referring to the drawings, FIG. 1 is a flowchart of an exemplary body type specific information management method. The flowchart includes an authenticate user step 10, a new user step 20, a determine body info step 30, a store body info in profile step 40, a determine/store body type step 50, a lookup body type specific info step 60 and a provide body type specific info step 70. The method uses user profiles component 80 to store user profile data 90 and body type specific info component 90 to store body type specific information 95. In alternative embodiments, the components, steps, and information operate using various configurations. Operationally the method will first authenticate user 10, and it is determined if the user is a new user 20. If the user is new, the step to determine body info 30 ensues, followed by the step to store body info in profile 40, and the step to determine/store body type 50. Regardless of the outcome of the new user step 20, the step to lookup body type specific info 60 occurs next, followed by the step to provide body type specific info 70.

Figure 2:
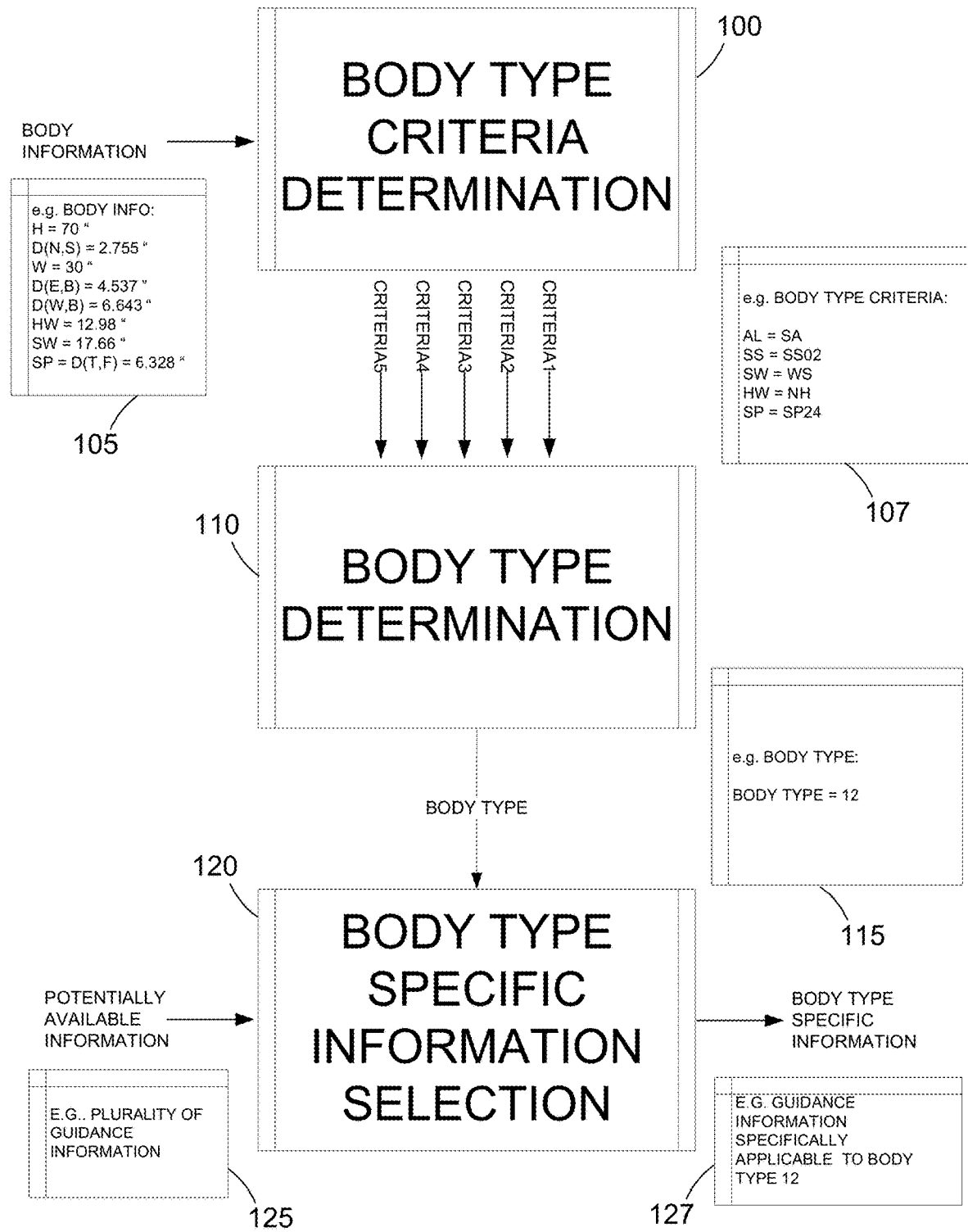
FIG. 2 is a block diagram of an exemplary body type specific information management system.

FIG. 2 is a block diagram of an exemplary body type specific information management system. The block diagram includes a body type criteria determination component 100, a body type determination component 110, and a body type specific information selection component 120. Operationally, body information 105 such as the e.g. information illustrated, is utilised by the body type criteria determination component 100 to determine criteria 1-5 such as the e.g. body type criteria 107 illustrated: AL=(Arms Length=Average Arms)=AA, SS=(Shoulder Slant)=SS02, SW=(Shoulder Width=Wide Shoulders)=WS, HW=(Hip Width=Narrow Hips)=NH, SP=(Shoulder Projection)=SP24. The body type criteria 1-5 are then used in turn by the body type determination component 110 to determine a body type, such as the e.g. body type 115 illustrated. The body type is then used by the body type specific information selection component 120 to select from potentially available information such as e.g. plurality of guidance information 125 to provide body type specific information such as e.g. guidance information 127 specifically applicable to the determined e.g. body type.

Figure 3:
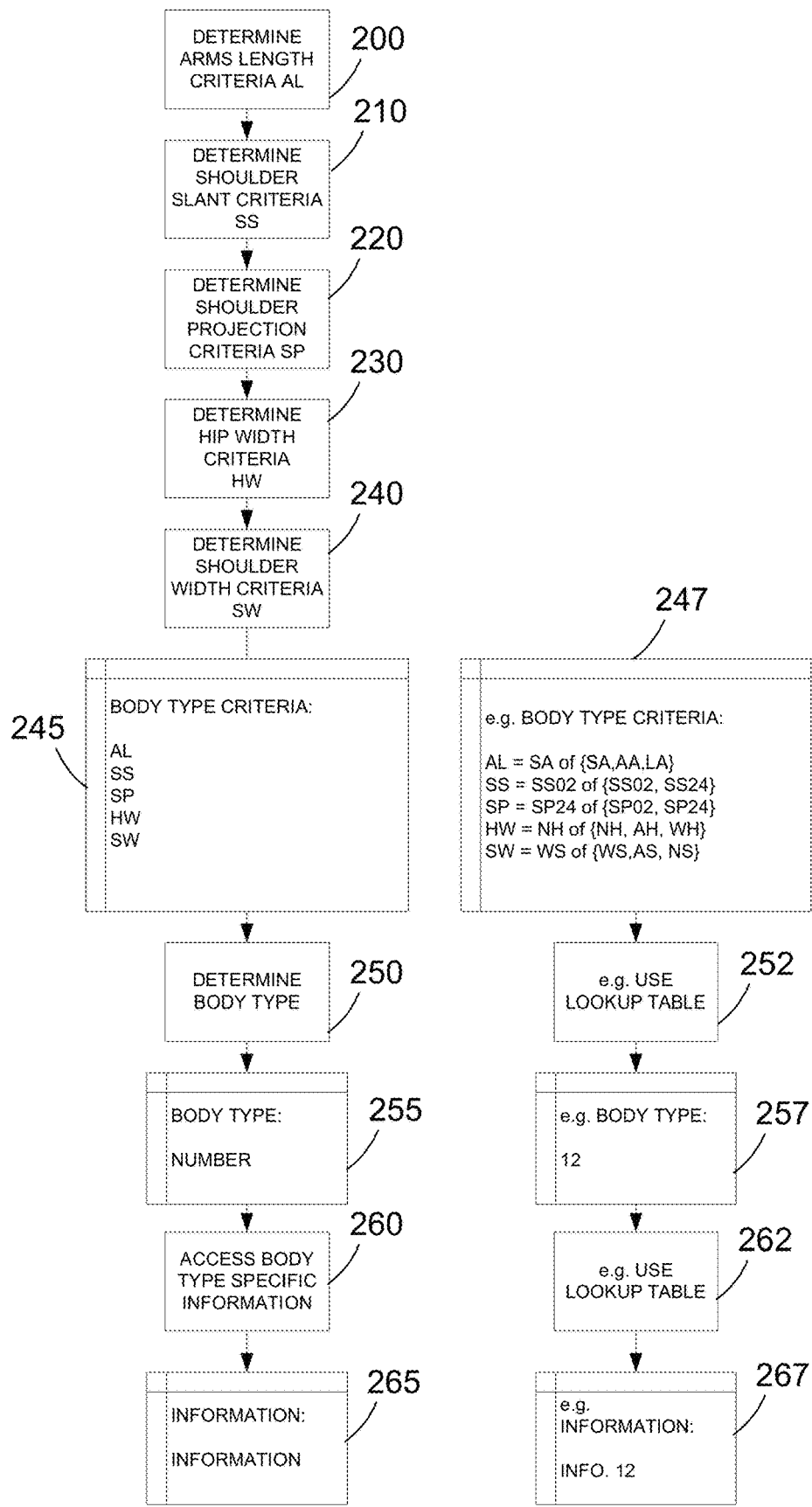
FIG. 3 is a flowchart of exemplary steps to determine exemplary body type criteria and exemplary body type.

FIG. 3 is a flowchart of exemplary steps to determine exemplary body type criteria and exemplary body type. The flowchart includes and goes through a determine arms length criteria AL step 200, determine shoulder slant criteria SS step 210, a determine shoulder projection criteria SP step 220, a determine hip width criteria HW step 230, a determine shoulder width criteria SW step 240, a determine body type step 250, and an access body type specific information step 260. As illustrated the exemplary body type criteria 245 includes generally AL, SS, SP, HW and SW and as illustrated in one example 247 has values of SA, SS02, SP24, NH and WS selected from ranges of values (SA,AA,LA), (SS02, SS24), (SP02,SP24), (NH,AH,WH), (WS,AS,NS) resulting in an e.g. 3×2×2×3×3=108 e.g. possible body types e.g. in a lookup table 252. As illustrated the exemplary body type is shown as a number 255 and as illustrated in one example has value 257 of 12. As illustrated the exemplary information accessed 260 e.g. using lookup table 262 and includes information 265 and in one example 267 has a value of INFO 12.

Figure 4:
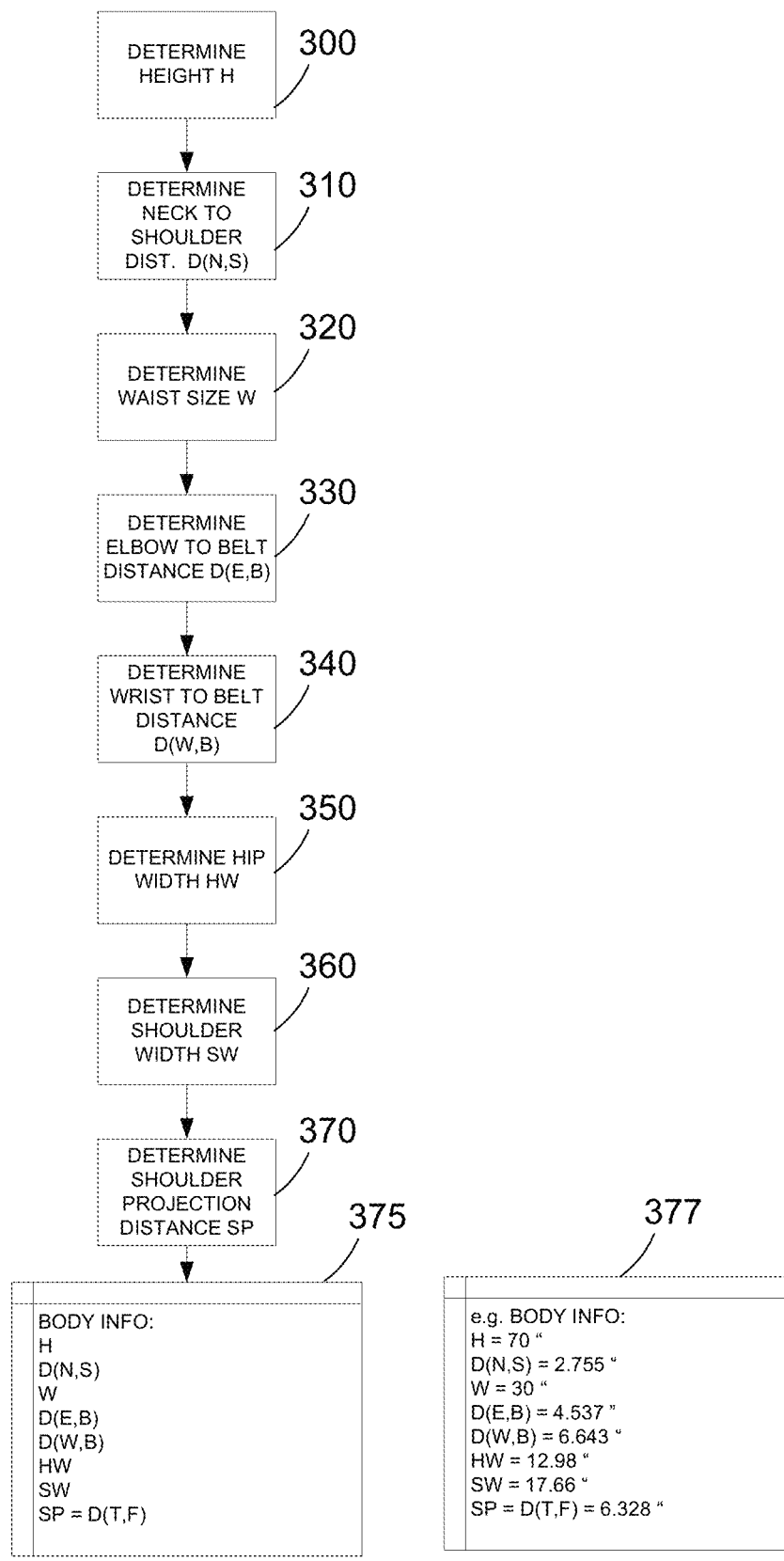
FIG. 4 is a flowchart of exemplary steps to determine exemplary body information.

FIG. 4 is a flowchart of exemplary steps to determine exemplary body information. The flowchart includes and goes through a determine height H step 300, determine next to shoulder dist. D(N,S) step 310, a determine waist size W step 320, a determine elbow to belt distance D(E,B) step 330, a determine wrist to belt distance D(W,B) step 340, a determine hip width HW step 350, a determine shoulder width SW step 360, and a determine shoulder projection distance SP step 370. As illustrated the flowchart provides body 375 info that includes the determined H, D(N,S), W, D(E,B), D(W,B), HW, SW and SP=D(T,F) and as illustrated e.g. values in inches 377 for those body info.

Figure 5:
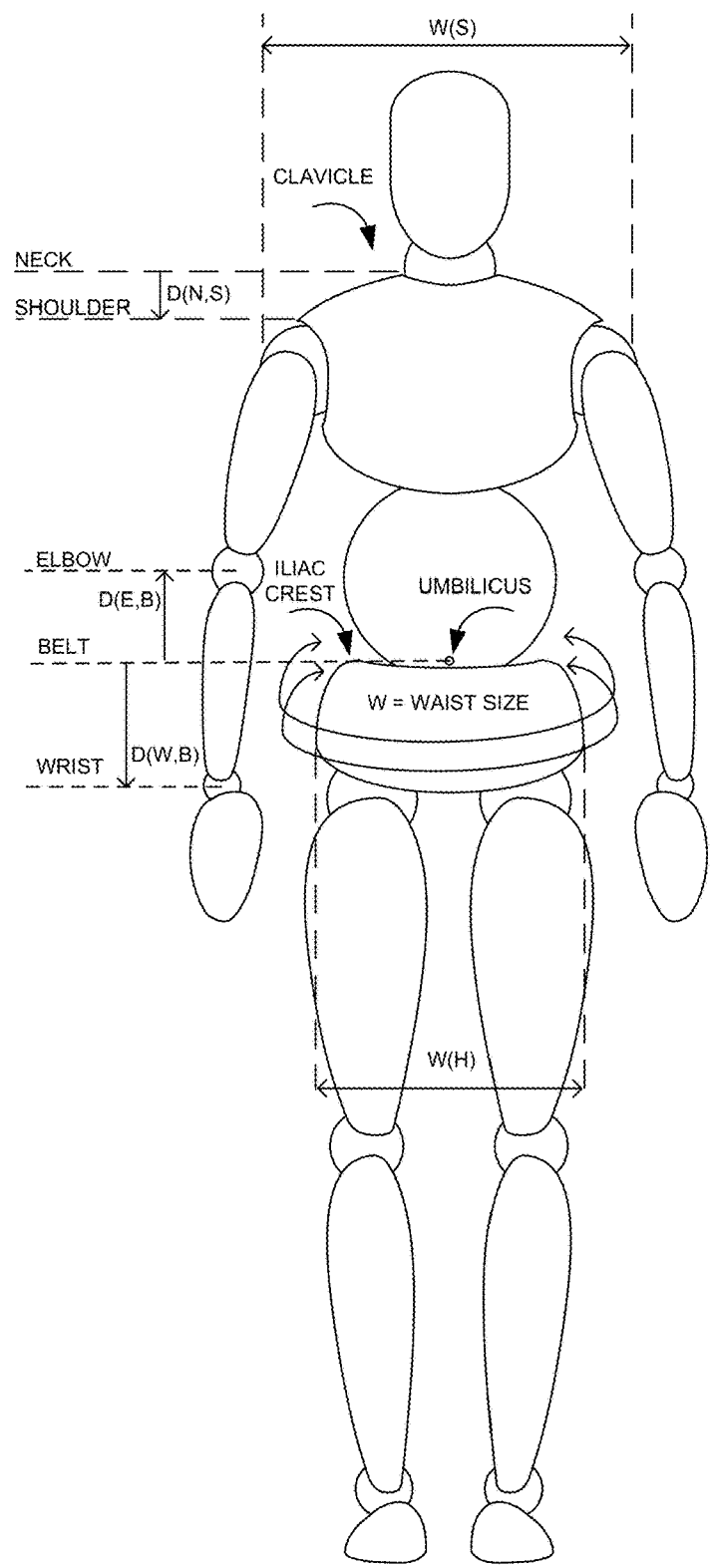
FIG. 5 is an illustration of a model of a person showing exemplary body information.

FIG. 5 is an illustration of a model of a person showing exemplary body information. As shown in the model, three points are used to represent two measurements. The position of the belt line, which is substantially coincidental with a line passing through the iliac crest and the umbilicus of the model, is used as a reference for measuring distance. The position of elbow relative to the belt line is used to measure D(E,B). The position of the wrist relative to the belt line is used to measure D(W,B). The position of the shoulder relative to the neck line is used to measure D(N,S). The waist size W is illustrated and substantially corresponds to the waist size of pants that would fit the model. The width of the hips W(H) of the model is measured as is the width of the shoulders W(S) of the model.

Figure 6:
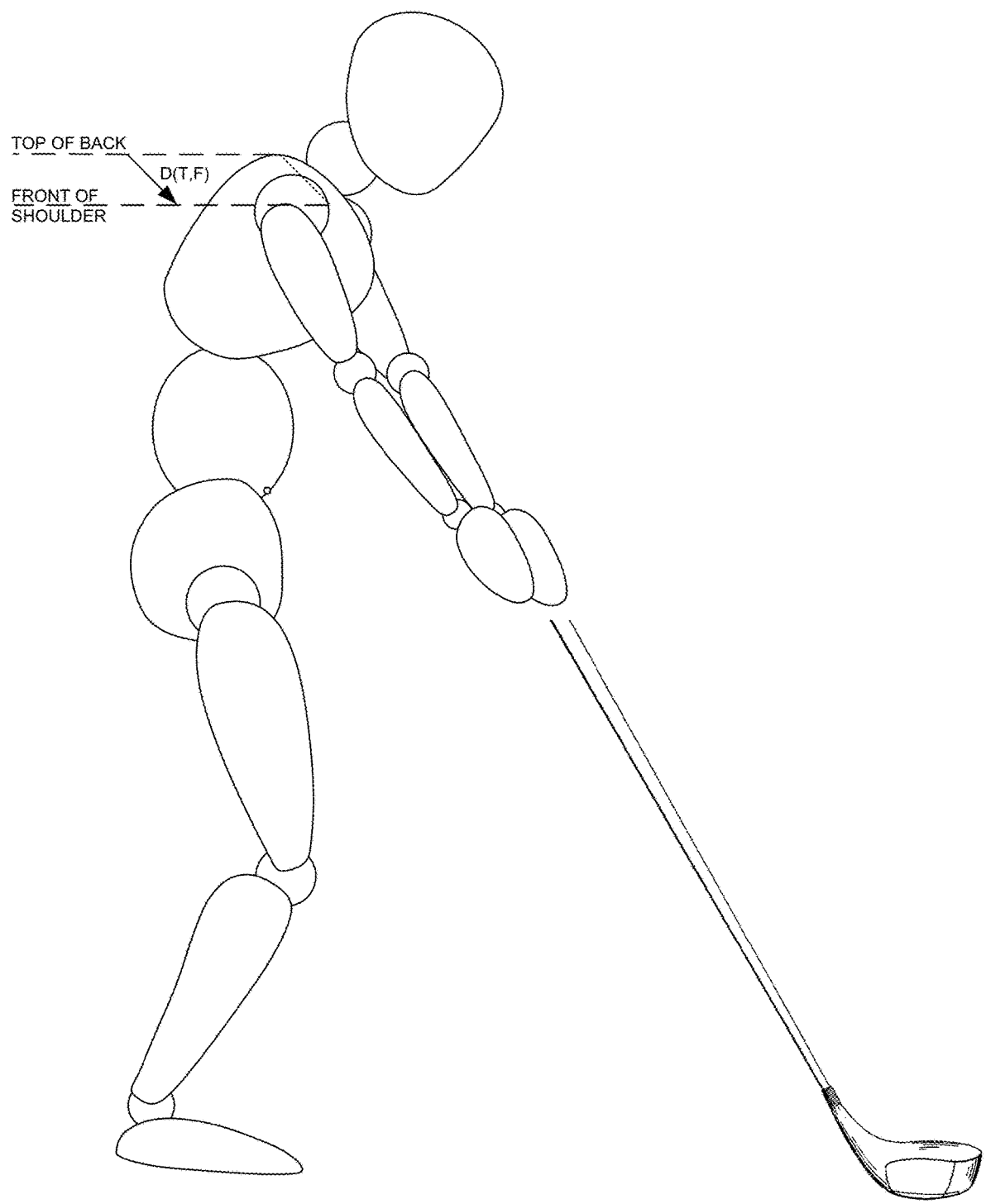
FIG. 6 is an illustration of a model of a person showing exemplary shoulder body information.

FIG. 6 is an illustration of a model of a person showing exemplary shoulder body information. The top of the back is used as a reference for measuring distance. The position of the front of the shoulder relative to the top of the back is used to measure D(T,F). The position of the neck line, which is substantially at the juncture of the neck and the top of the clavicle, is used as a reference for measuring distance.

Figures 7, 8:
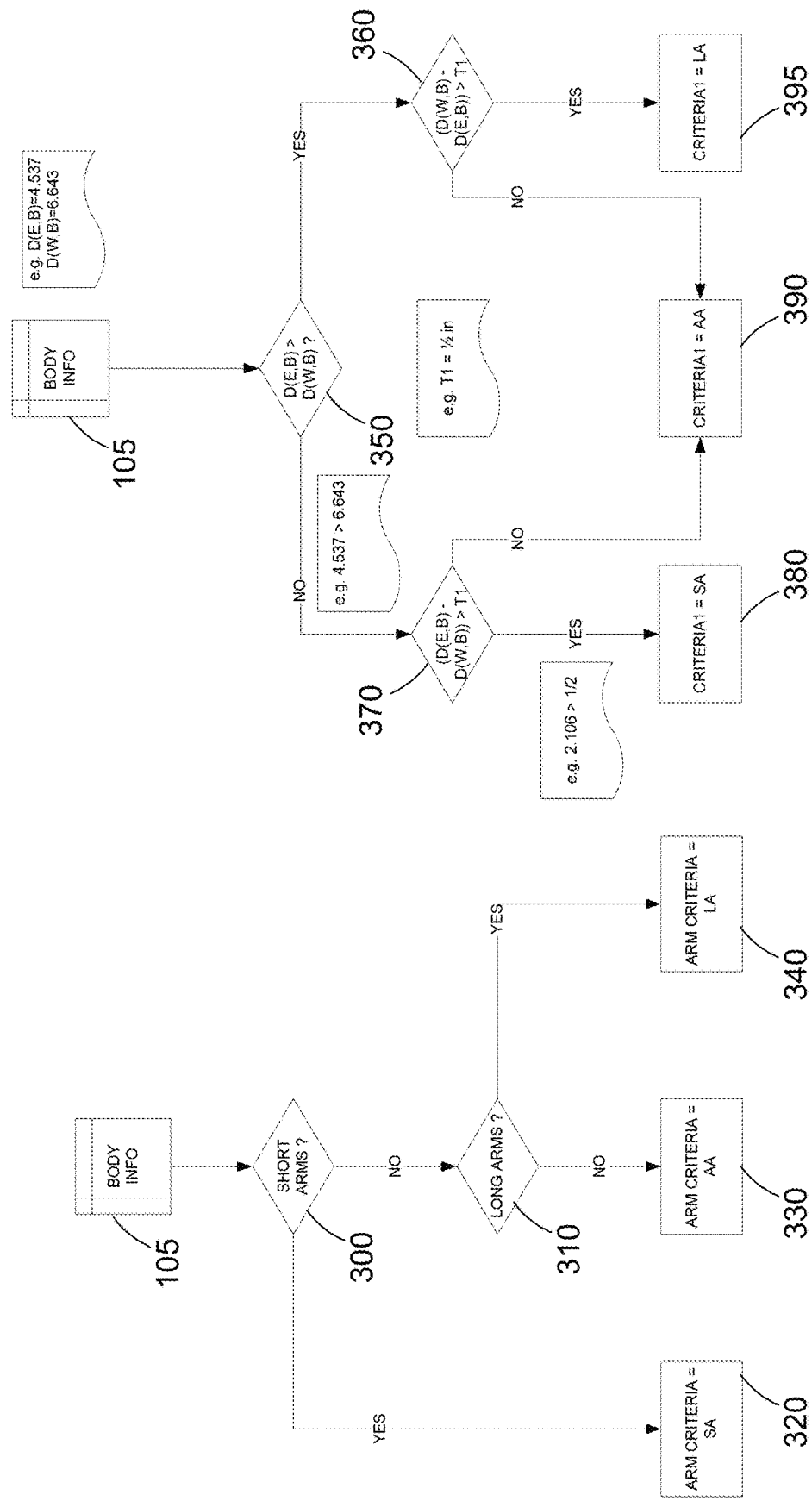
FIG. 7 is a flowchart of exemplary steps to determine arm criteria using arm body information.
FIG. 8 is an illustration of a flowchart of exemplary steps to determine the first criteria of FIG. 7 using the exemplary arm body information of FIG. 5.

FIG. 7 is a flowchart of exemplary steps to determine arm criteria using arm body information. The flowchart includes a short arms step 300 and a long arms step 310 as well as an arm criteria=SA step 320, an arm criteria=AA step 330 and an arm criteria=LA step 340. Body info 105 is used to determine if the body info includes short arms 300. If so determined, the arm criteria is set to SA 320. If not so determined, the long arms step 310 ensues to determine if the Body info 105 includes long arms. If so determined, arm criteria is set to LA 340. If Body info 105 does not include short arms or long arms then the arm criteria is set to AA 330.

FIG. 8 is an illustration of a flowchart of exemplary steps to determine the first criteria of FIG. 7 using the exemplary arm body information of FIG. 5. The steps include determining if D(E,B)>D(W,B) 350, determining if the difference between D(E,B) and D(W,B) is greater than a threshold T1 360 such as e.g. T1=½ in, determining if the difference between D(W,B) and D(E,B) is greater than a threshold T1 370, setting criteria1=SA 380, setting criteria2=AA 390, and setting criteria3=LA 395. Operationally body information 105 such as e.g. D(E,B) and D(W,B) information illustrated, is used by the D(E,B)>D(W,B) step 350. If it is determined that D(E,B) is greater than D(W,B), then the difference between D(E,B) and D(W,B) is compared to threshold T1 at the D(E,B)−D(W,B)>T1 370 step. If so determined, then the criteria1=SA step 380 ensues. This is what would happen if the steps are used with the e.g. body info 105 illustrated. If however D(E,B) is not greater than D(W,B), then if the difference between D(W,B) and D(E,B) is greater than T1 360, then the criteria1=LA step 395 ensues. If the absolute difference between D(W,B) and D(E,B) is not greater that T1, then the criteria1=AA step ensues 390.

Figure 9:
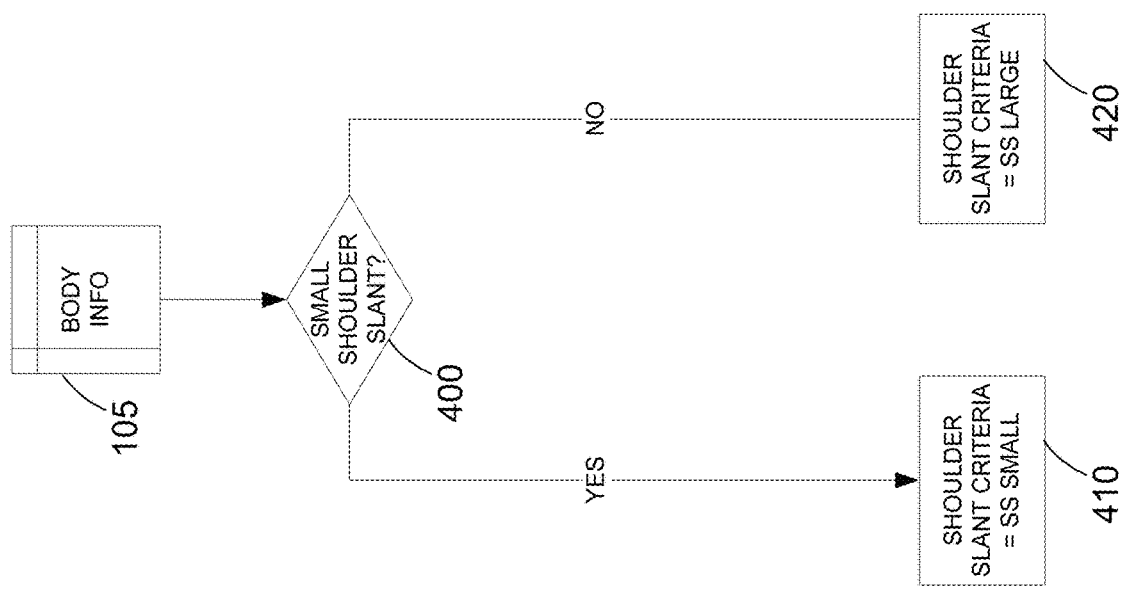
FIG. 9 is an illustration of a flowchart of exemplary steps to determine shoulder slant criteria using shoulder body information.

FIG. 9 is an illustration of a flowchart of exemplary steps to determine shoulder slant criteria using shoulder body information. The flowchart includes a small shoulder slant determination step 400, a shoulder slant criteria=sss small step 410 and a shoulder slant criteria=ss large step 420. Body info is used by the small shoulder slant determination step to determine if the body info includes small shoulder slant. If so determined the shoulder slant criteria=ss small step occurs, alternatively the shoulder slant criteria=ss large step occurs.

Figure 10:
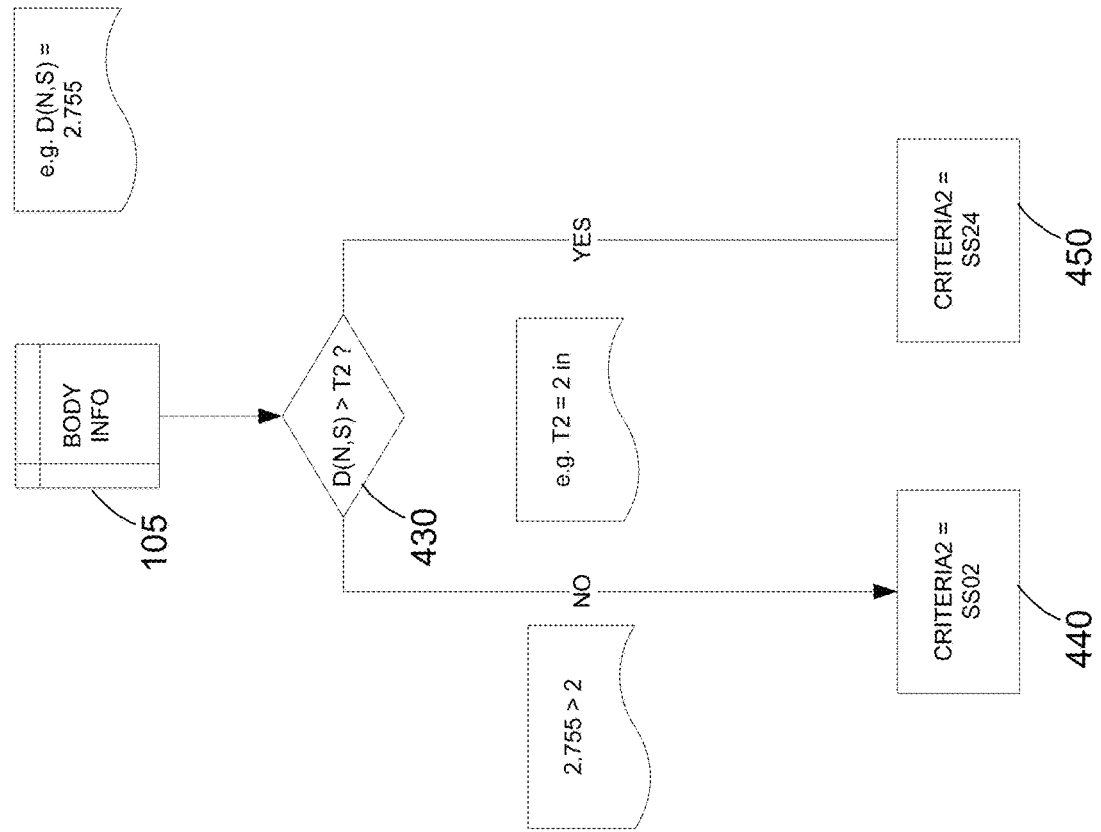
FIG. 10 is an illustration of a flowchart of exemplary steps to determine the second criteria of FIG. 9 using the exemplary shoulder body information of FIG. 5.

FIG. 10 is an illustration of a flowchart of exemplary steps to determine the second criteria of FIG. 9 using the exemplary shoulder body information of FIG. 5. The flowchart includes a D(N,S)>T2 determination step 430, a criteria2=SS02 step 440, and a criteria2=SS24 step 440. Operationally, Body info 105 such as e.g. D(N,S)=2.755 in the D(N,S)>T2 step and compared to a threshold T2 such as e.g. 2 in. If it is determined that D(N,S) is greater than T2, then the criteria2=SS02 step occurs, as is the case with the e.g. Alternatively, the criteria2=SS24 step ensues.

Figures 11, 12:
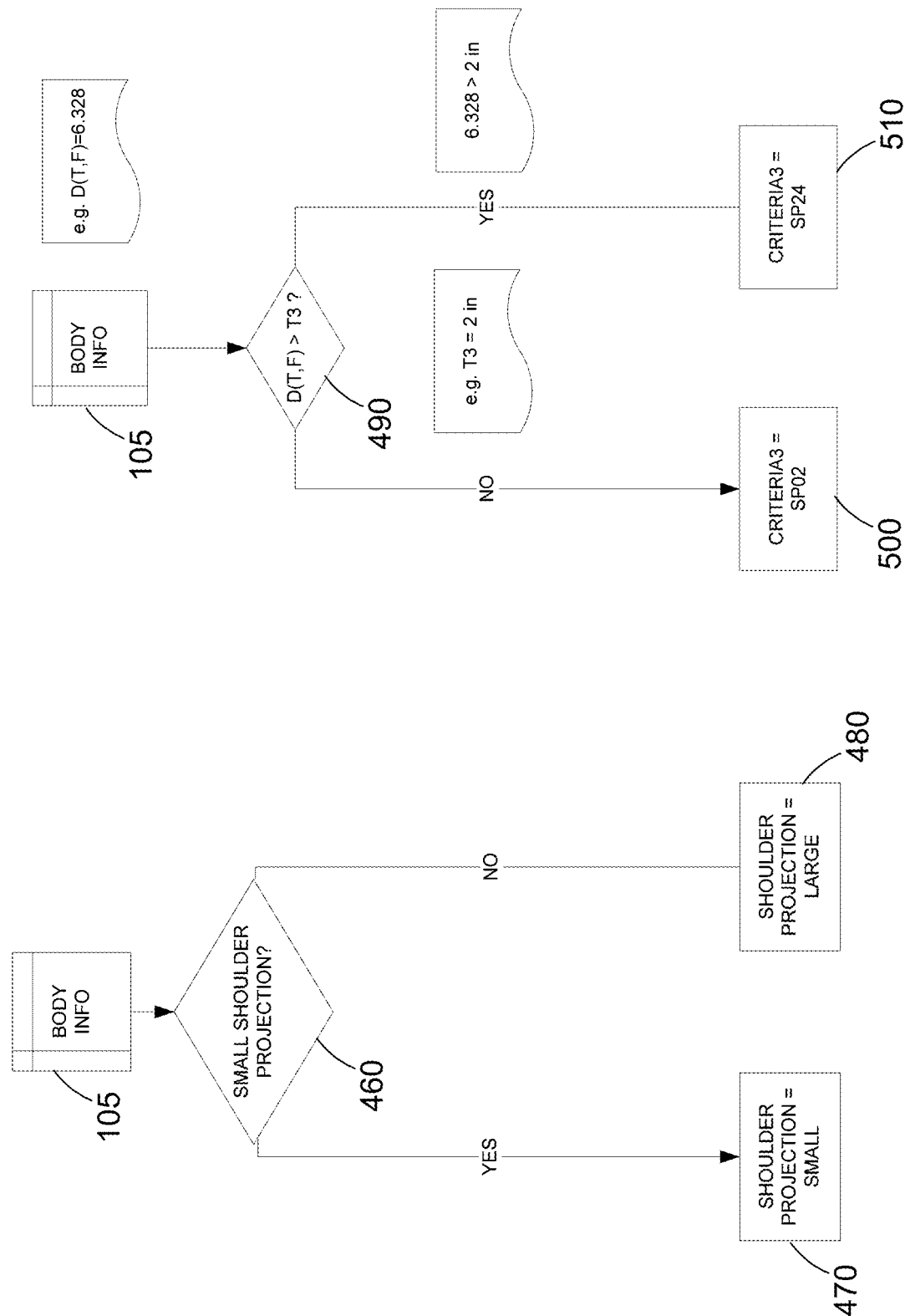
FIG. 11 is an illustration of a flowchart of exemplary steps to determine shoulder projection criteria using shoulder body information.
FIG. 12 is an illustration of a flowchart of exemplary steps to determine the third criteria of FIG. 11 using the exemplary shoulder body information of FIG. 6.

FIG. 11 is an illustration of a flowchart of exemplary steps to determine shoulder projection criteria using shoulder body information. The flowchart includes a small shoulder projection determination step 460, a shoulder projection=small 470 and a shoulder projection=large step 480. Operationally, Body info 105 is used by the small shoulder projection determination step to determine if Body info includes small shoulder projection. If so determined, the shoulder projection=small step ensures, alternatively the shoulder projection=large step ensues.

FIG. 12 is an illustration of a flowchart of exemplary steps to determine the third criteria of FIG. 11 using the exemplary shoulder body information of FIG. 6. The flowchart includes a D(T,F)>T3 determination step 490, a criteria3=SP02 step 500 and a criteria3=SP24 step 510. Operationally, body info 105 such as e.g. D(T,F)=6.328, is compared to a threshold T3 such as e.g. 2 in. If it is determined that D(T,F) is greater than the threshold T3, then step criteria3=SP24 ensues, as with the e.g. Alternatively step criteria3=SP02 ensues.

FIG. 13 is an illustration of a flowchart of exemplary steps to determine hip width criteria using hip body information. The flowchart includes a narrow hips determination step 520, a wide hips determination step 530, a hips criteria=NH step 540, a hips criteria=AH step 550, and a hips criteria=WH step 560. Body info 105 is used by the narrow hips determination step and if so determined the hips criteria=NH step ensues. Alternatively, the wide hips determination step ensues. If so determined, then hips criteria=WH step ensues. Alternatively, the hips criteria=AH step ensues.

FIG. 14 is an illustration of a flowchart of exemplary steps to determine the fourth criteria of FIG. 13 using the exemplary hip body information of FIG. 5. The flowchart includes a W<T4N determination step 570, a W>T4W determination step 580, a criteria 4=NH step 590, a criteria4=AH step 600, and a criteria4=WH step 610. Operationally, Body info 105 such as e.g. W=30 in is compared to threshold T4N e.g. 34 in at the W<T4N determination step. If so determined, the criteria4=NH step ensues. Alternatively, the W>T4W determination step ensues and if so determined the criteria4=WH step ensues, or alternatively the criteria4=AH step ensues.

Figures 15, 16:
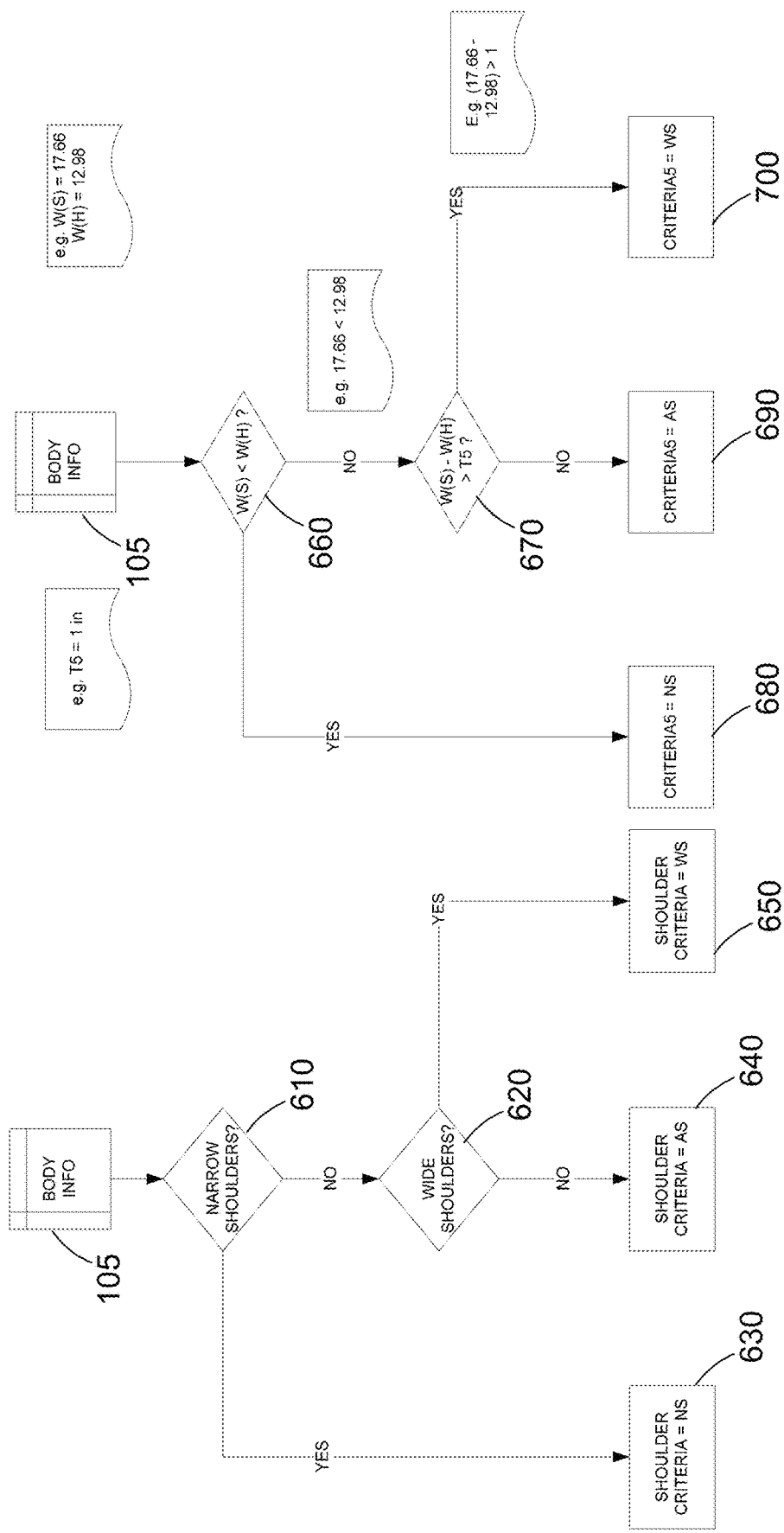
FIG. 15 is an illustration of a flowchart of exemplary steps to determine shoulder width criteria using shoulder body information.
FIG. 16 is an illustration of exemplary steps to determine the fifth criteria of FIG. 16 using the exemplary shoulder body information of FIG. 5.

FIG. 15 is an illustration of a flowchart of exemplary steps to determine shoulder width criteria using shoulder body information. The flowchart includes a narrow shoulders determination step 610, a wide shoulders determination step 620, a shoulder criteria=NS step 630, a shoulder criteria=AS step 640, and a shoulder criteria=WS step 650. Operationally body info 105 is used by the narrow shoulder determination step, and if so determined the shoulder criteria=NS step ensues. Alternatively, the wide shoulders determination step ensues. If so determined, the shoulder criteria=WS step ensues. Alternatively, the shoulder criteria=AS step ensues.

FIG. 16 is an illustration of exemplary steps to determine the fifth criteria of FIG. 16 using the exemplary shoulder body information of FIG. 5. The flowchart includes a W(S)<W(H) determination step 660, a W(S)−W(H)>T5 determination step 670, a criteria5=NS step 680, a criteria5=AS step 690 and a criteria5=WS step 700. Body info 105 such as e.g. W(S)=17.66 and W(H)=12.98 is used by the W(S)>W(H) determination step, and if so determined the criteria5=NS step ensues. Alternatively, as in the e.g., step W(S)−W(H)>T5 step ensues. If the difference between W(S) and W(H) is greater than threshold T5, such as is the case if e.g. T5 is 1 in, then step criteria5=WS ensues. Alternatively, step criteria5=AS ensues.

FIG. 17 is an illustration of an exemplary beginning third of an exemplary body type specific information lookup table. As illustrated, the lookup table 252A maps a range of values of criteria 1-5, each corresponding to body type 115 number 1-36, to information 95 1-36. The example values for criteria 1-5 correspond to body type 12 and information 12.

FIG. 18 is an illustration of an exemplary middle third of an exemplary body type specific information lookup table. As illustrated, the lookup table 252B maps a range of values of criteria 1-5, each corresponding to body type 115 number 37-72, to information 95 37-72.

FIG. 19 is an illustration of an exemplary ending third of an exemplary body type specific information lookup table. As illustrated, the lookup table 252C maps a range of values of criteria 1-5, each corresponding to body type 115 number 73-108, to information 95 73-108.

FIG. 20 is an exemplary information record structure including body type specific information structure. As illustrated for a given set of criteria 1-5, an info #125 includes basic setup guidance, basics guidance, takeaway/backswing/Impact guidance, finish guidance, and body type specific guidance. As illustrated this includes guidance G1-G24. It is anticipated that the specific number and kind of guidance can be varied and any such variation is contemplated to be within the scope of the present application. As illustrated, reference to N videos, as well as an expected aspect of the body type are also included in the information record structure.

FIG. 21 is an exemplary information record data including body type specific information data. In this example, the guidance G1-G24, the expectation, and N videos are all specific to the body type #12 127 used in the e.g. of the flowcharts and user interface.

FIG. 22 is an illustration an exemplary user interface for determining exemplary body information without the need for photographs. In this interface 800, all of the measurements required to determine body type are requested from the user. This could be used, for example, by a user that requests custom measurement at a service provider such as a golf store or golf club, or by using a measuring tape, or by using an electronic device to determine the required information. Additional optional information is collected, such as foot size.

FIG. 23 is an illustration an exemplary user interface for determining exemplary body information using photographs. In this interface 900, not all of the measurements required to determine body type are requested from the user. Instead, some or all of the measurements are obtained from photographs provided by the user. This could be used, for example, by a user that requests custom measurement by taking a photograph using a mobile device or camera and uploading the files over the internet. Additional optional information is collected, such as foot size. Operationally, the digital images provided by the user can be processed either automatically or with user interaction. An overview of the steps the user must take, e.g. two examples of photos that are required to be taken by the user in order to obtain the measurements using the interface, are presented to the user. The user is instructed to take the two photos. The user is instructed to upload the first forward facing photo. The user is asked to confirm the picture or to choose a new picture, such as for example, if the picture is rotated 90 degrees, or is the wrong picture. In some embodiments, the user is instructed to place dots on the top of the head in the picture, and the bottom of the foot. Two photo instructions can illustrate what is required. The user can be enabled to place a dot on the head by clicking or touching the top of the head in the picture. The user can be enabled to place a dot on the feet by clicking or touching near the bottom of the feet in the picture, such as for example where the optional golf ball was placed while taking the picture. The user can be prompted to enter their height. This value, along with the two points, establishes a scale for determining distances using points on the pictures. The user can be shown the body information collected so far, and is asked to either move to the next step, or to reset and select the points again to establish the reference scale. The shoulder slant is determined in an analogous way by placing points at the base of the neck and top of the shoulder. The belt line and waist size are determined in an analogous way. The length of the arms are determined in an analogous way. The hip width is determined in an analogous way. The width of the shoulder is determined in an analogous way. The user is instructed to upload the second profile photo. The shoulder projection is determined in an analogous way. In an automatic processing, the required information is extracted directly from the images by using, for example using machine vision.

Figure 24:
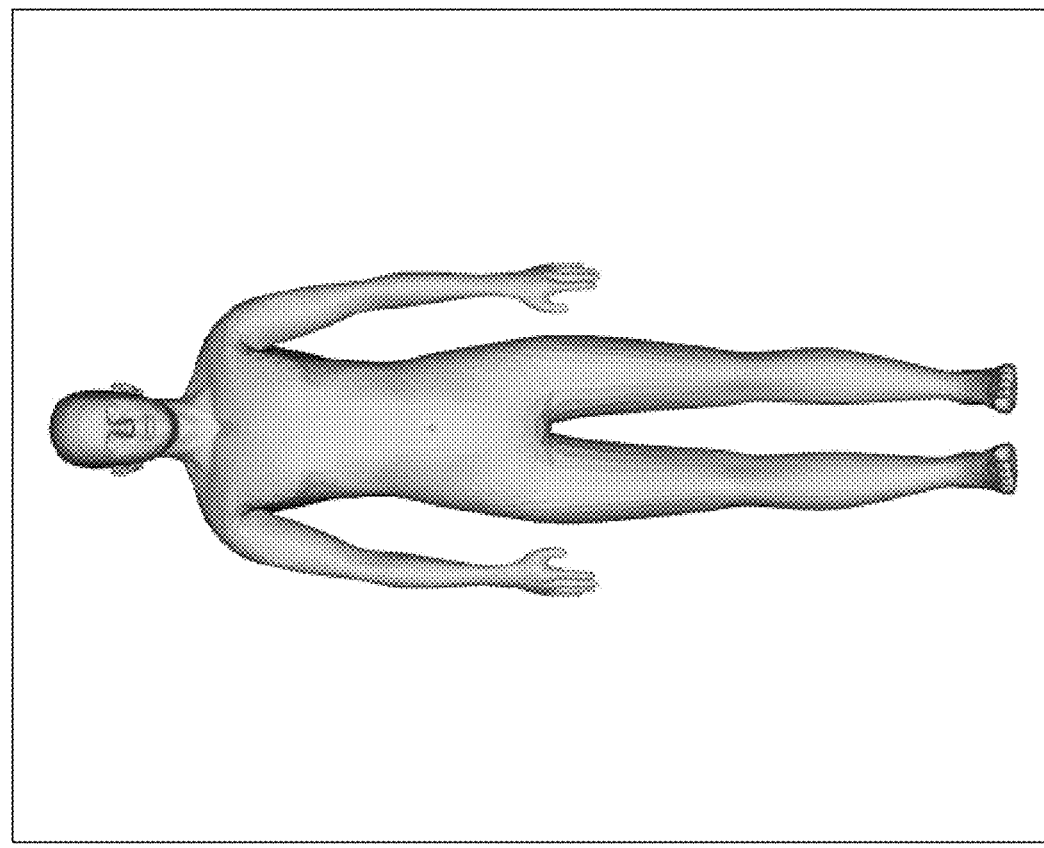
FIG. 24 is an illustration of an exemplary front facing picture of a person from which the exemplary body information of FIGS. 5, 7-10, and 13-16 can be determined.

FIG. 24 is an illustration of an exemplary front facing picture of a person from which the exemplary body information of FIGS. 5, 7-10, and 13-16 can be determined. An optional golf ball is placed between the ball of the feet of the person in order to provide a reference point for the ground and/or a scale factor. The front facing picture 910 can be analog or digital.

Figure 25:
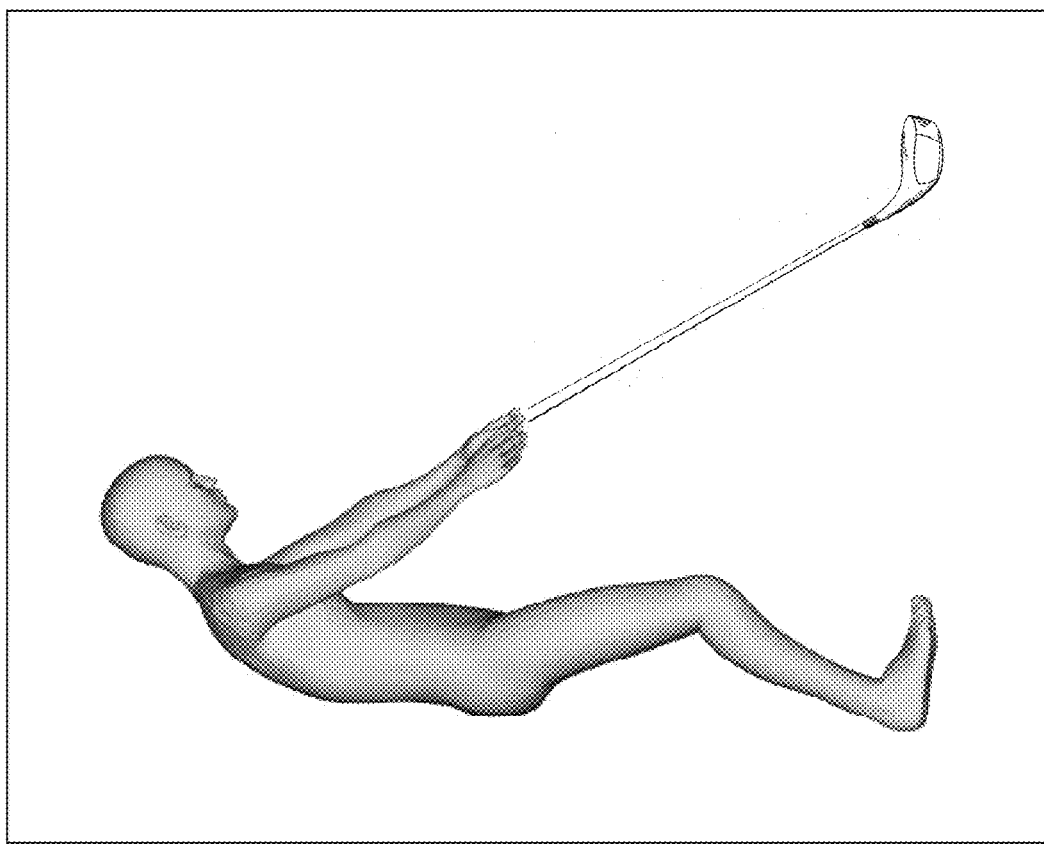
FIG. 25 is an illustration of an exemplary side stance picture of a person from which the exemplary body information of FIGS. 6, and 11-12 can be determined.

FIG. 25 is an illustration of an exemplary side stance picture of a person from which the exemplary body information of FIGS. 6, and 11-12 can be determined. An optional golf club is held by the person in order to facilitate the measurements in a normal starting position for golf. The side or golf stance picture 920 can be analog or digital.

Figure 26:
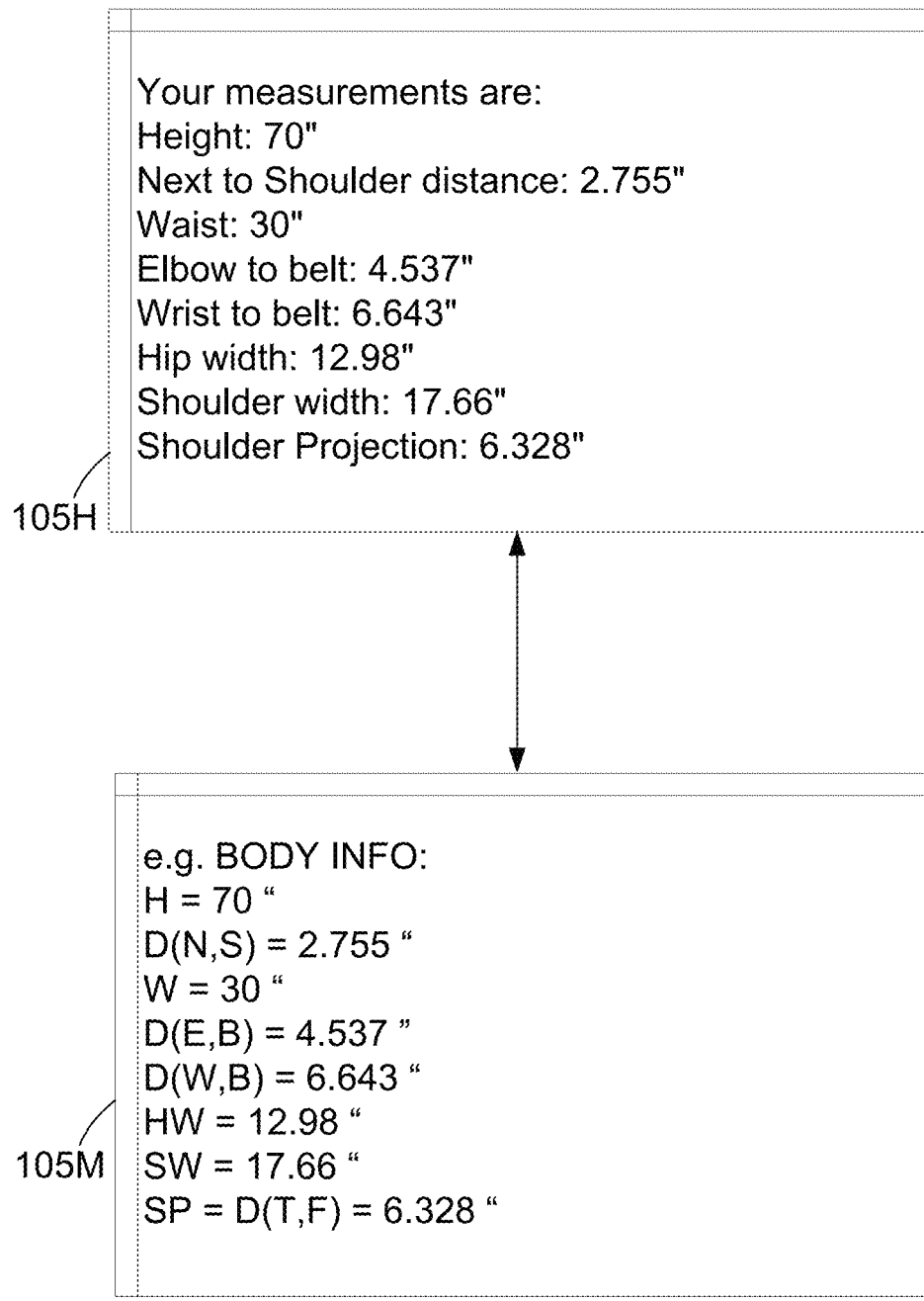
FIG. 26 illustrates the result of the use of the body type determination achieved using either user interaction or automation.

FIG. 26 illustrates the result of the use of the body type determination achieved using either user interaction or automation. The body information is illustrated in both machine usable 105M and human usable 105H forms. Once body information is determined, body type specific information is also derived or obtained in machine usable and human usable forms.

Figure 27:
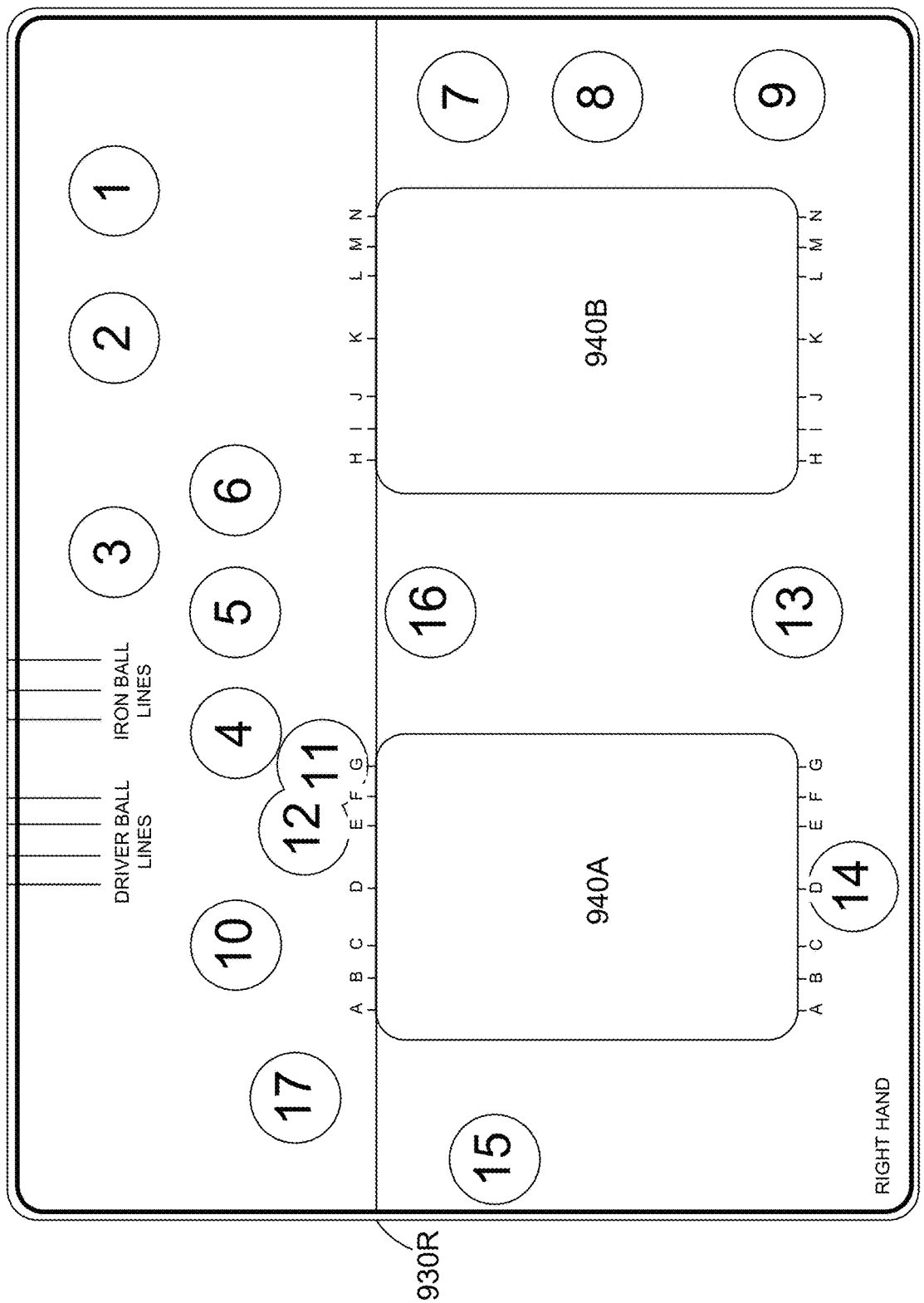
FIG. 27 is an illustration of a right hand side of an exemplary training carpet component of an apparatus to be used with body type specific information.

FIG. 27 is an illustration of a right hand side of an exemplary training carpet component of an apparatus to be used with body type specific information. As illustrated, the carpet includes 17 circular areas, each of which is approximately 3 inches in diameter, and in which are indicated respective indicia 1-17. Two rectangular areas parallel to the edges of the carpet are provided so a user of the carpet knows where to place their left and right feet. Each rectangular area has indicia at the top and bottom so as to facilitate the placement of the foot at the toe end and heel end respectively. As illustrated the left foot rectangular 940A are has indicia A-G and the right foot rectangular area 940B has indicia H-N. Four driver ball lines and three iron ball lines are illustrated perpendicularly to the top edge and nearer to the left edge so that a user knows where to place the golf ball. An indication that the carpet is for a right handed golfer is shown at the bottom left corner. Optionally, although not shown, the carpet is branded so as to direct the user to the appropriate system to obtain guidance on using the carpet for golf training. The guidance refers to the indicia on the carpet to provide guidance that is tailored to the specific body type of the golfer undergoing golf training.

Figure 28:
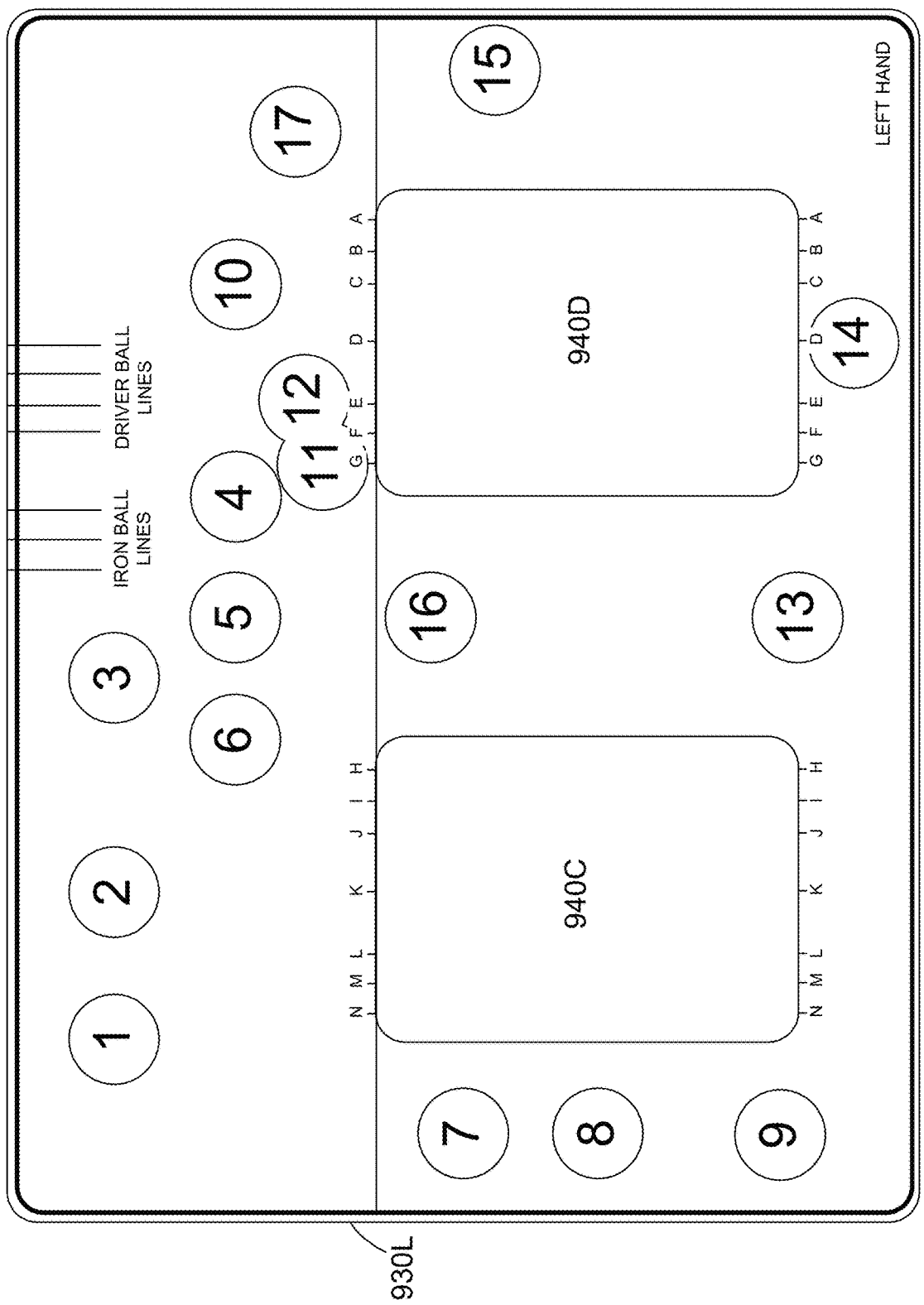
FIG. 28 is an illustration of a left hand side of an exemplary training carpet component of an apparatus to be used with body type specific information.

FIG. 28 is an illustration of a left hand side of an exemplary training carpet component of an apparatus to be used with body type specific information. The carpet is substantially a mirror image of FIG. 27, except that the left foot rectangular area 940C has indicia H-N and the right foot rectangular area 940D has indicia A-G.

In an alternative embodiment, a training carpet with only one side is used, either for a left handed golfer, or a right handed golfer. In a further alternative embodiment, augmented reality is used to present a virtual overlay of the carpet to the user, such as for example at a golf course or driving range.

Figure 29:
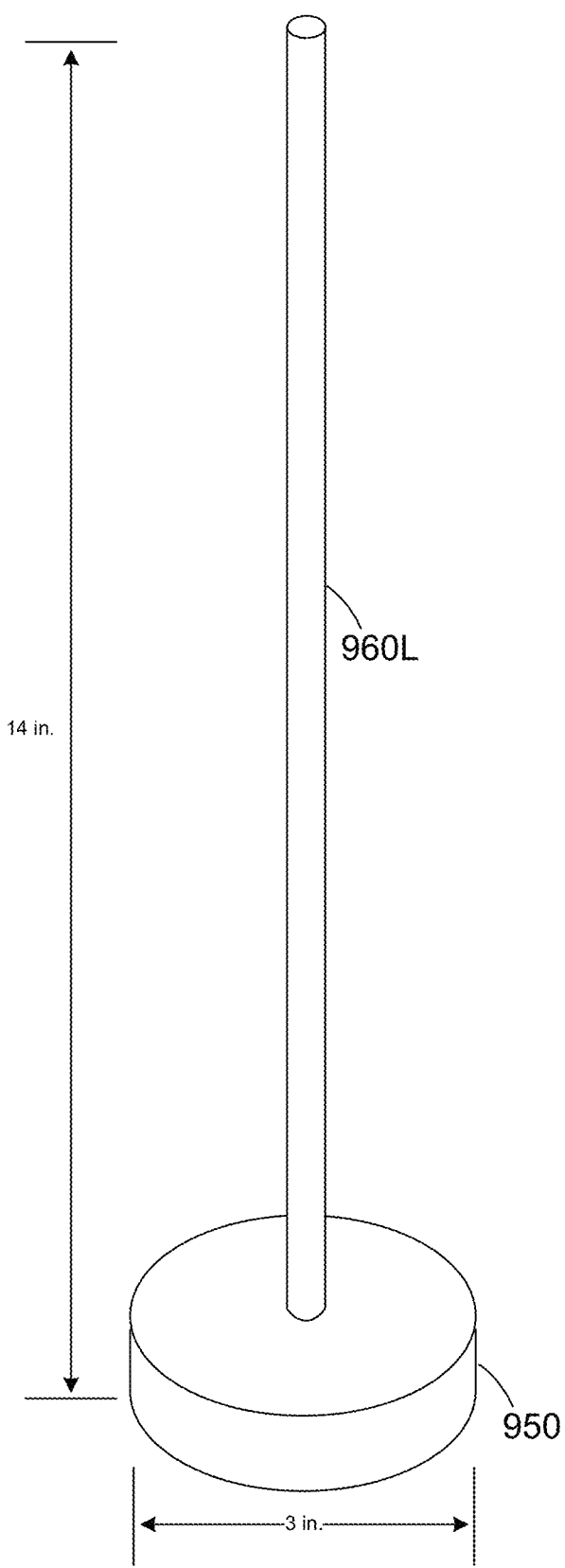
FIG. 29 is an illustration of an exemplary long peg component of an apparatus to be used with the body type specific information.

FIG. 29 is an illustration of an exemplary long peg component of an apparatus to be used with the body type specific information. The long peg includes a base 950 and a long stem 960L. As illustrated, the base of the long peg is 3 in, so as to coincide with the diameter of the circular areas of the carpets of FIGS. 64 and 65, such as for example a hockey puck. The long peg includes a stem which is inserted into a hole in the base such that the height of the peg is as illustrated 14 in. In alternative embodiments, bases of different diameters and pegs of different heights can be used.

Figure 30:
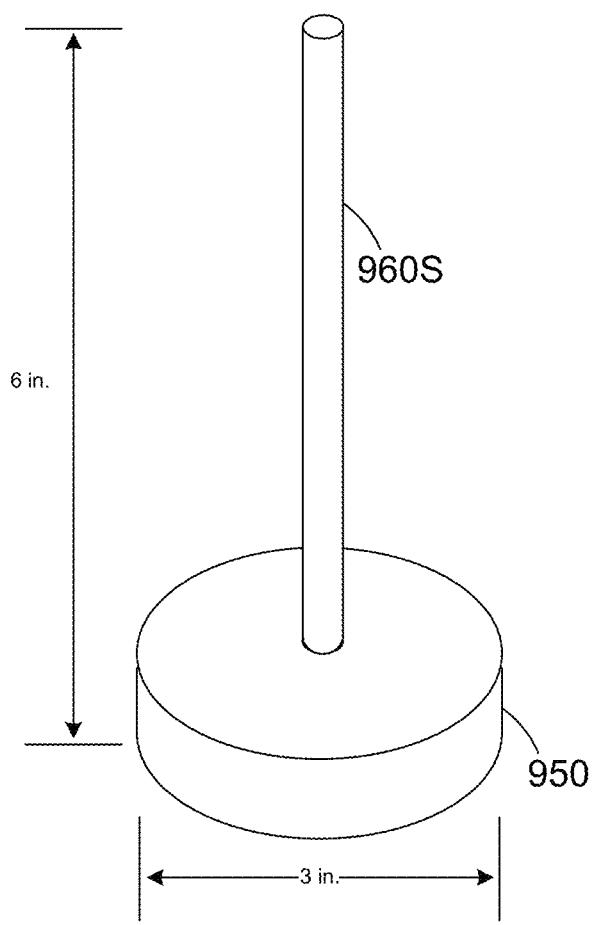
Figure 31:
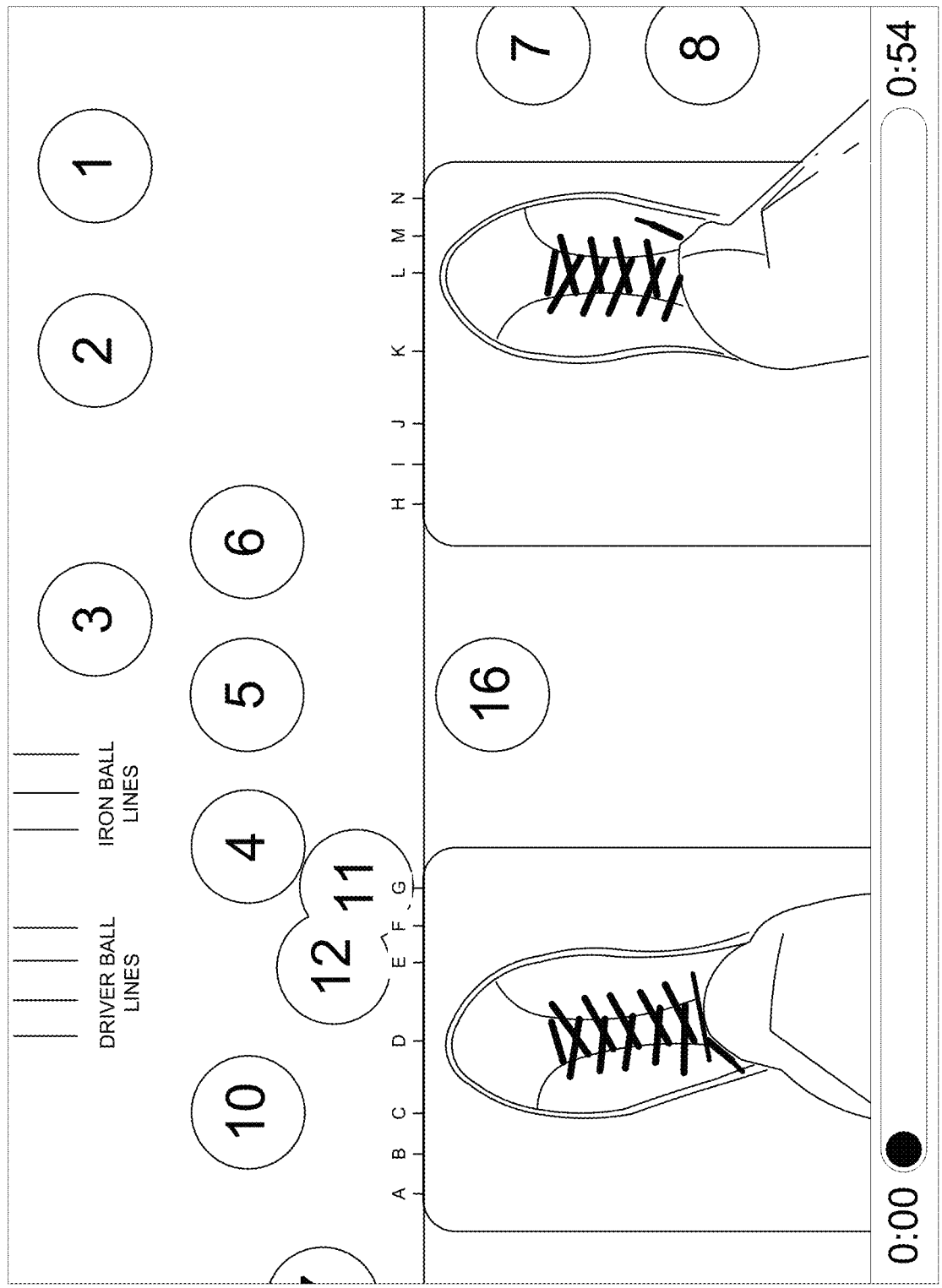
FIGS. 31-40 are illustrations of exemplary training guidance body type specific information provided using the exemplary method of FIG. 1, the exemplary system of FIG. 2, and the components of the apparatus of FIGS. 27-30.
Figure 32:
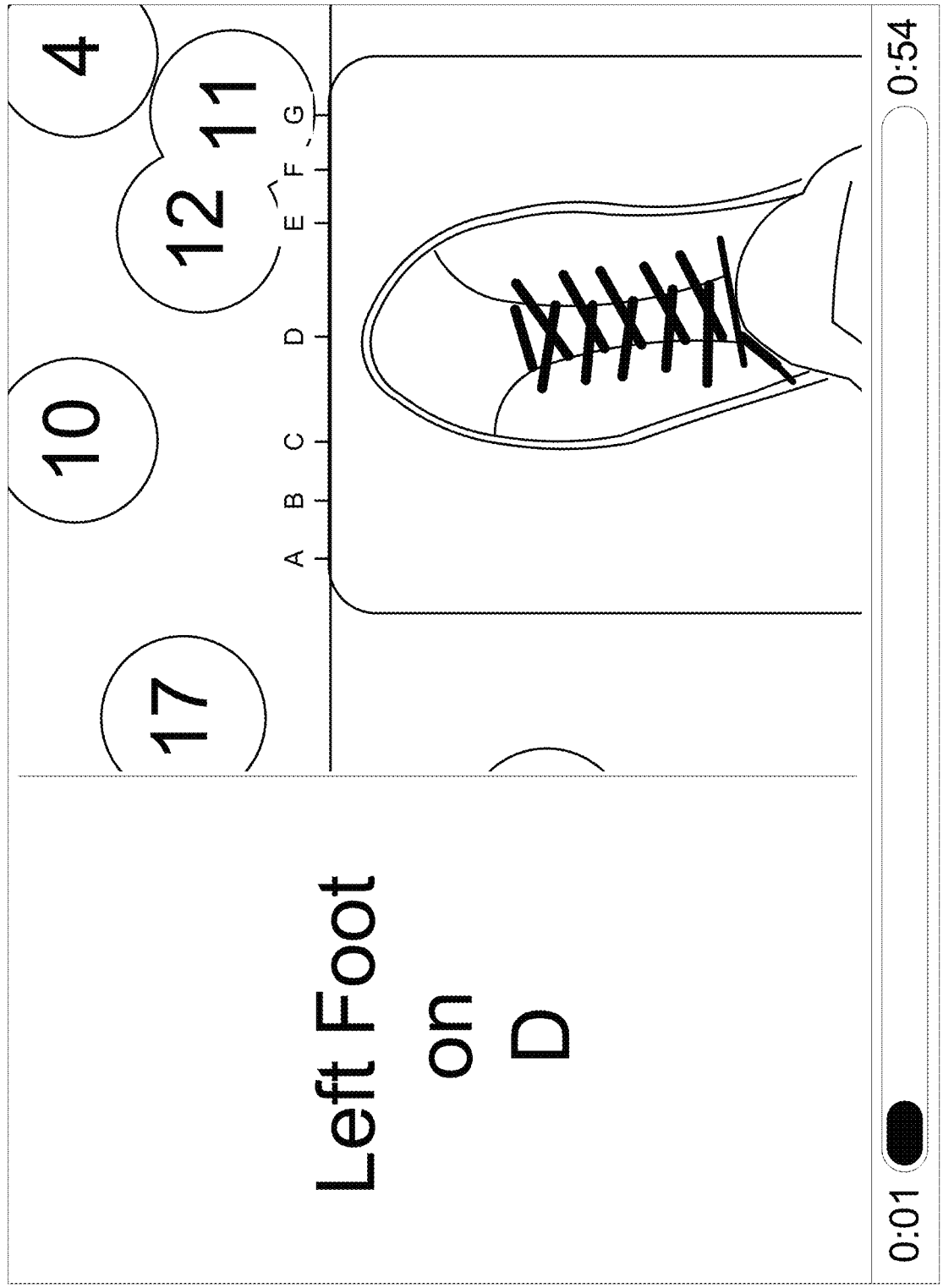
Figure 33:
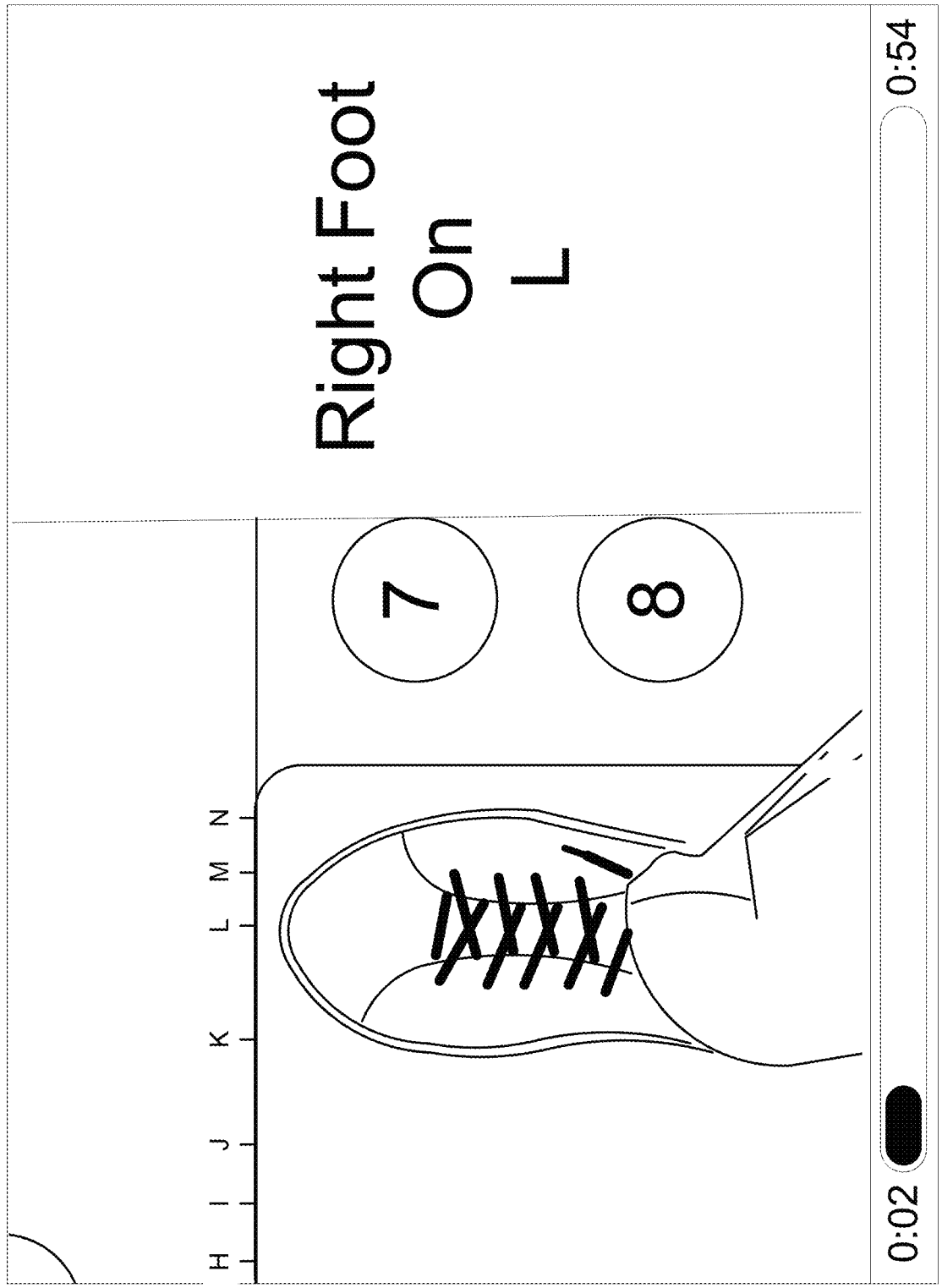
Figure 34:
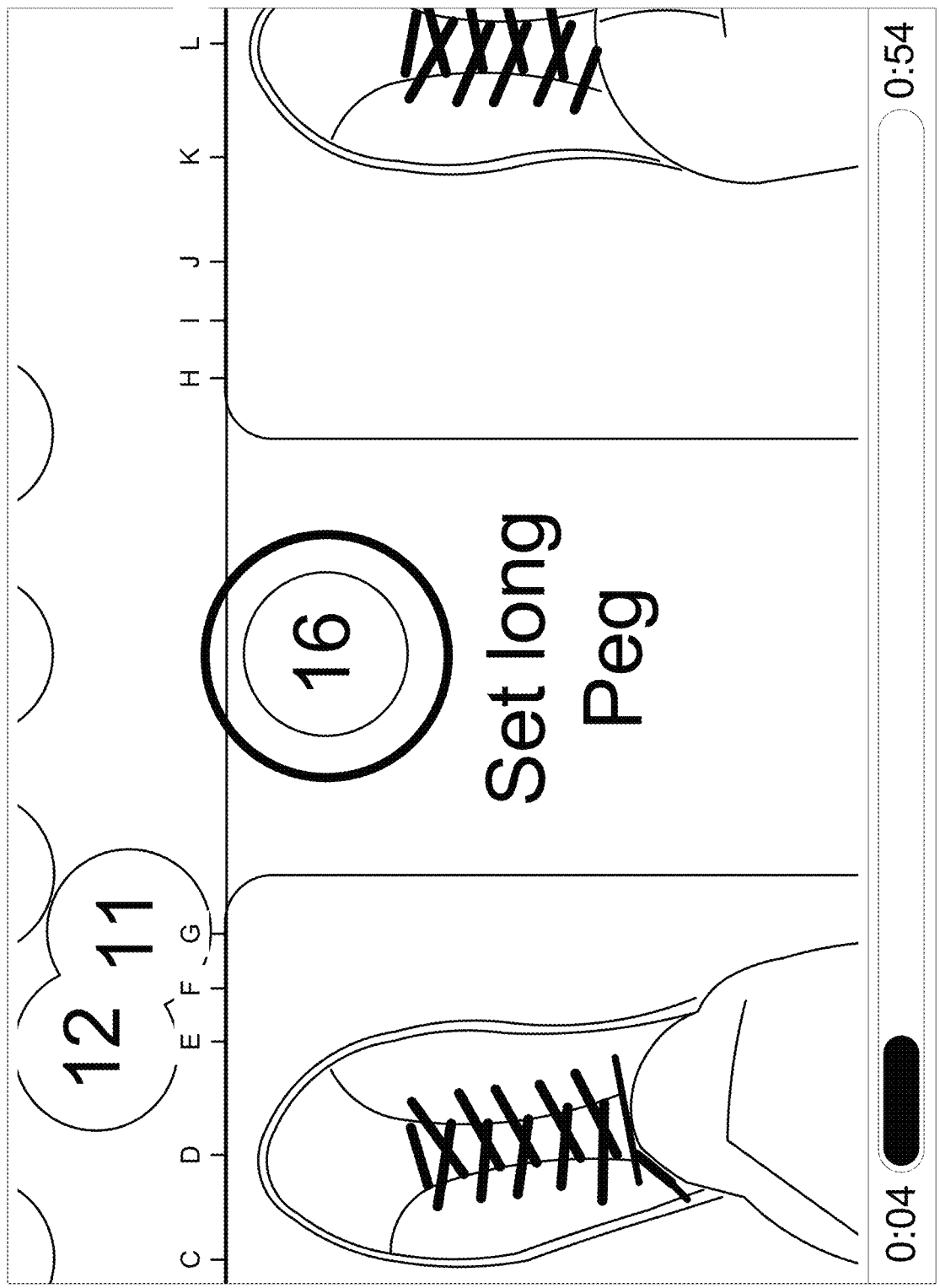
Figure 35:
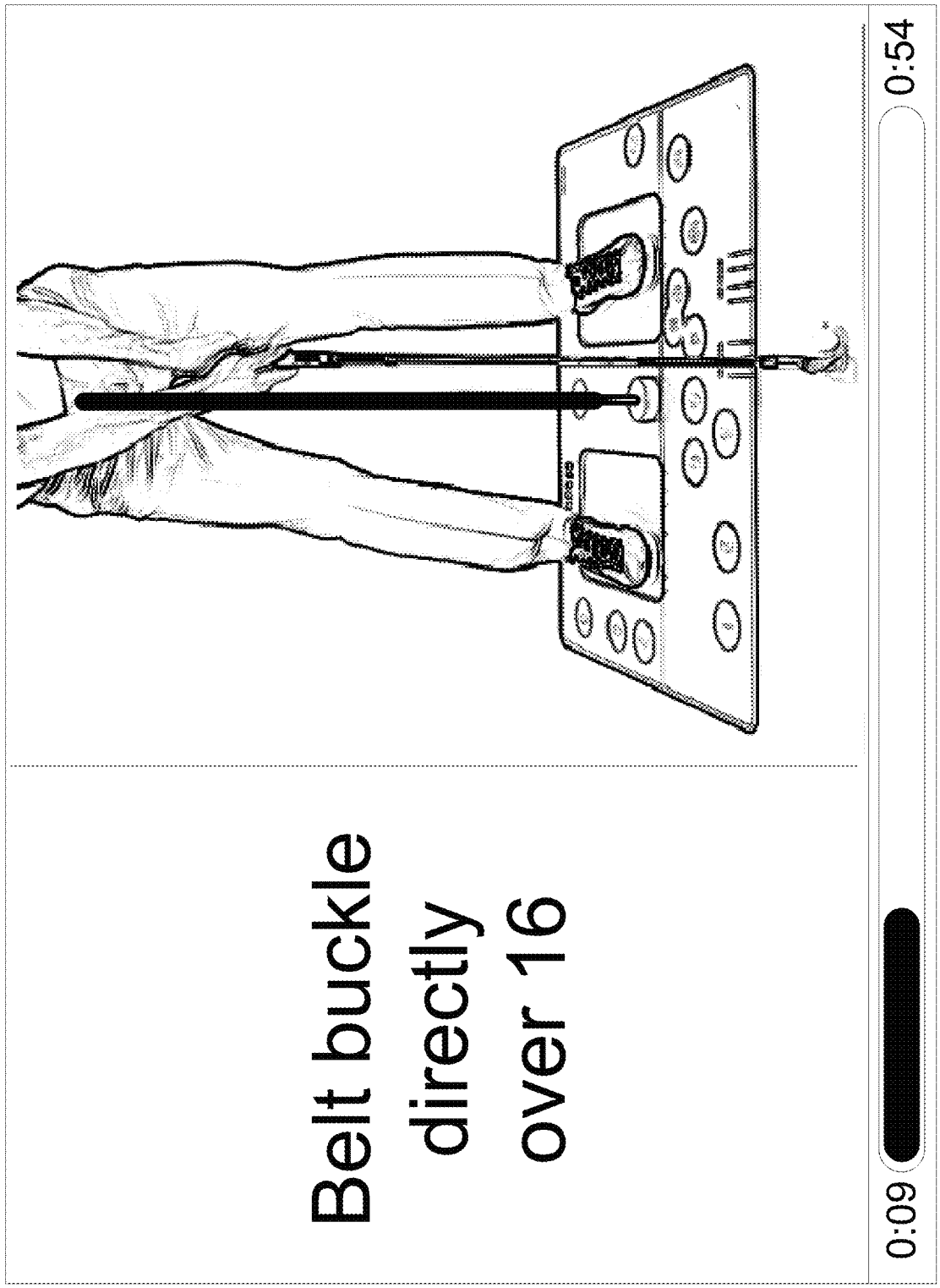
Figure 36:
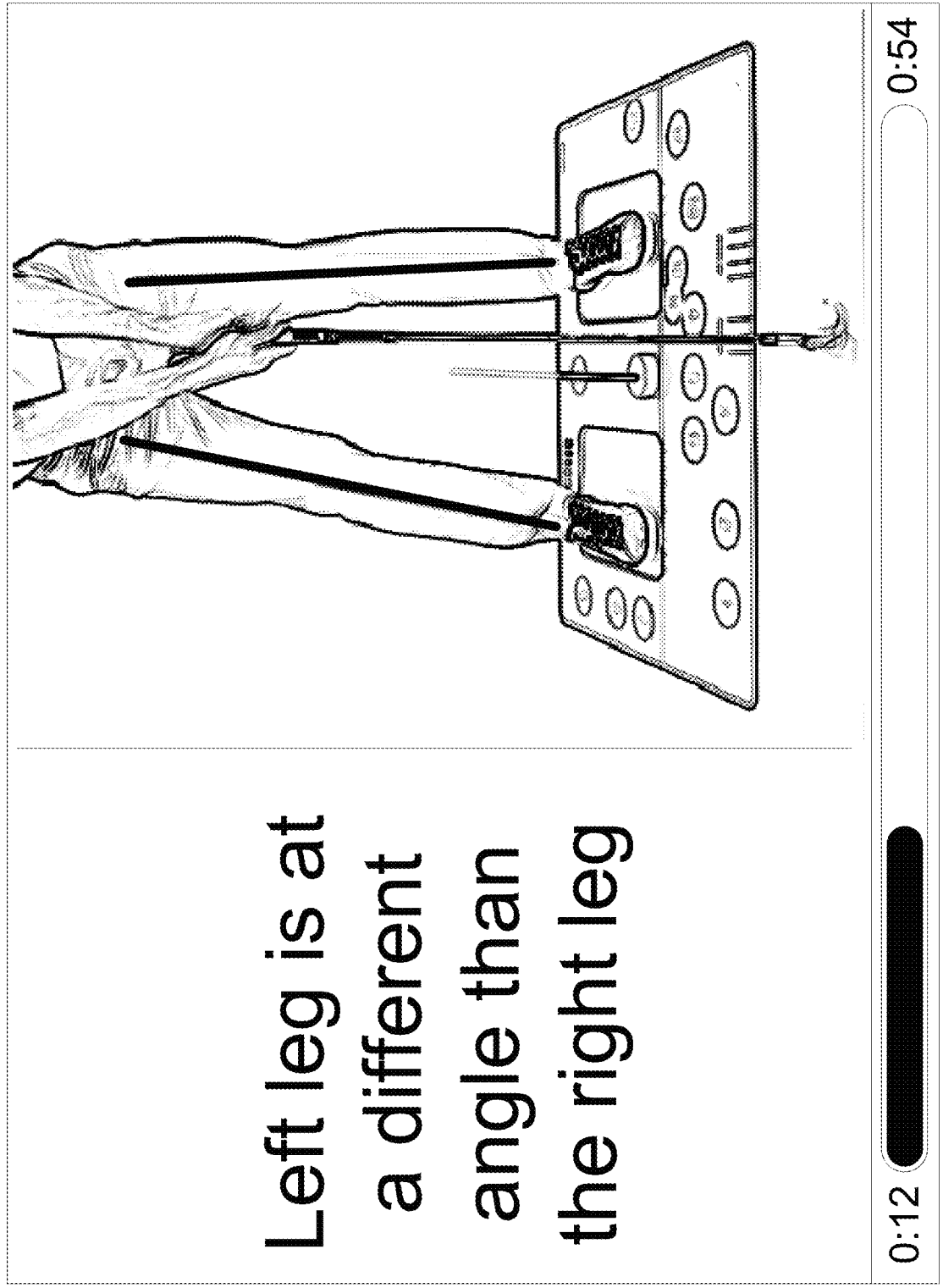
Figure 37:
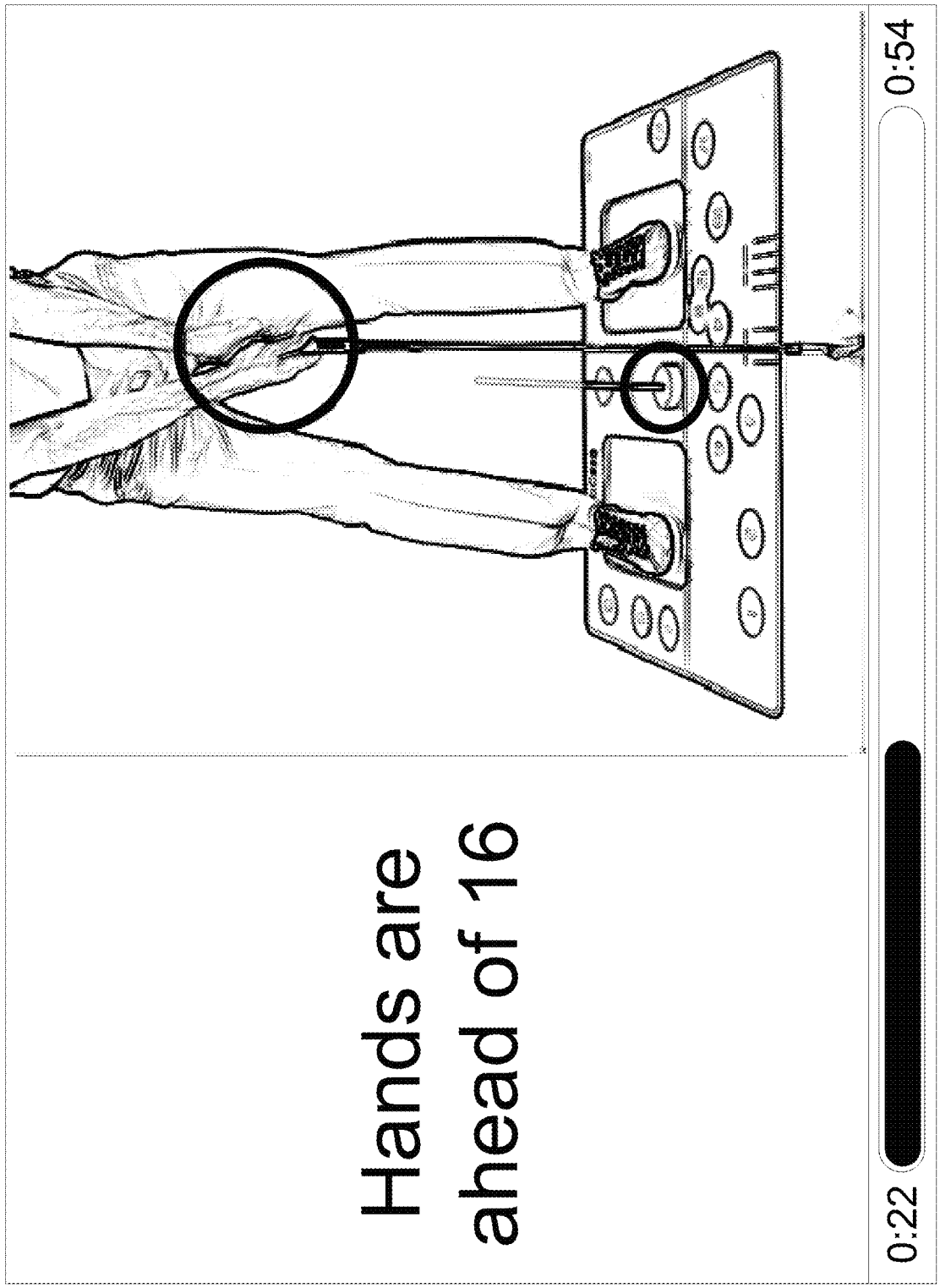
Figure 38:
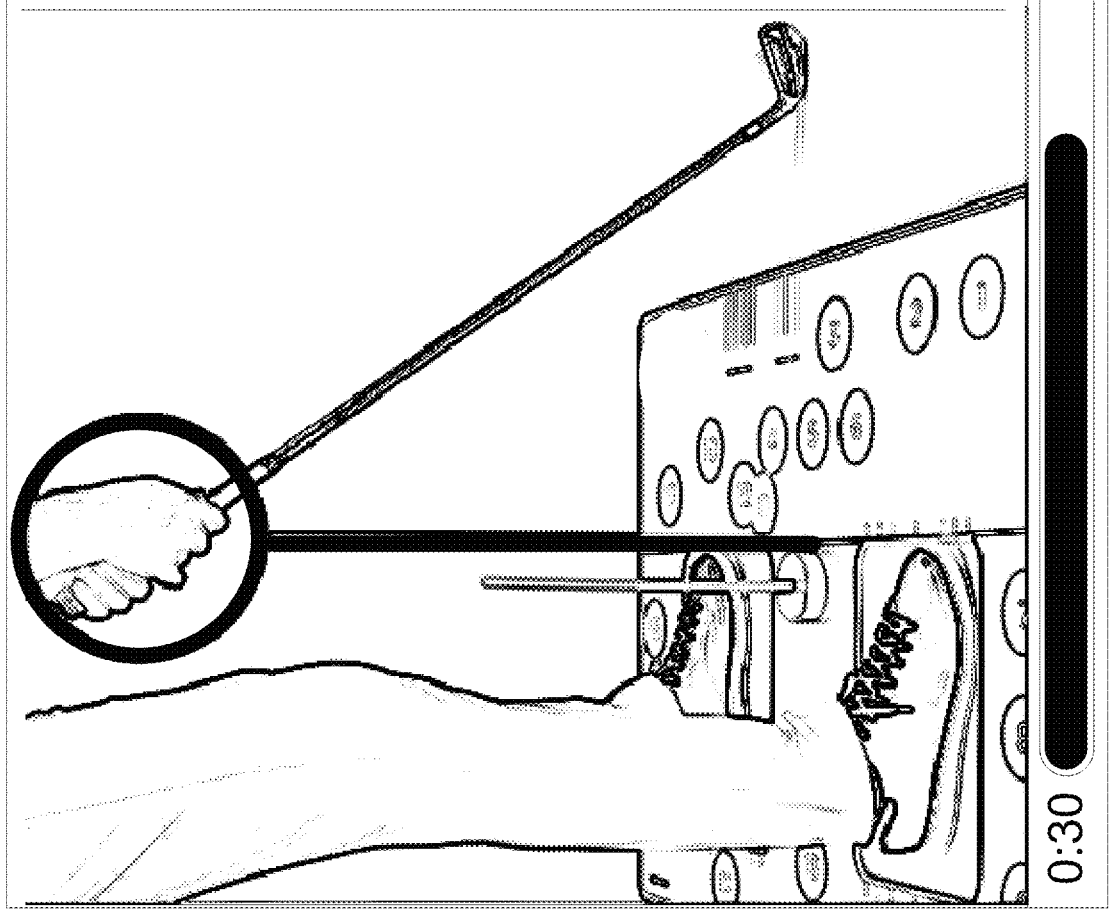
Figure 39:
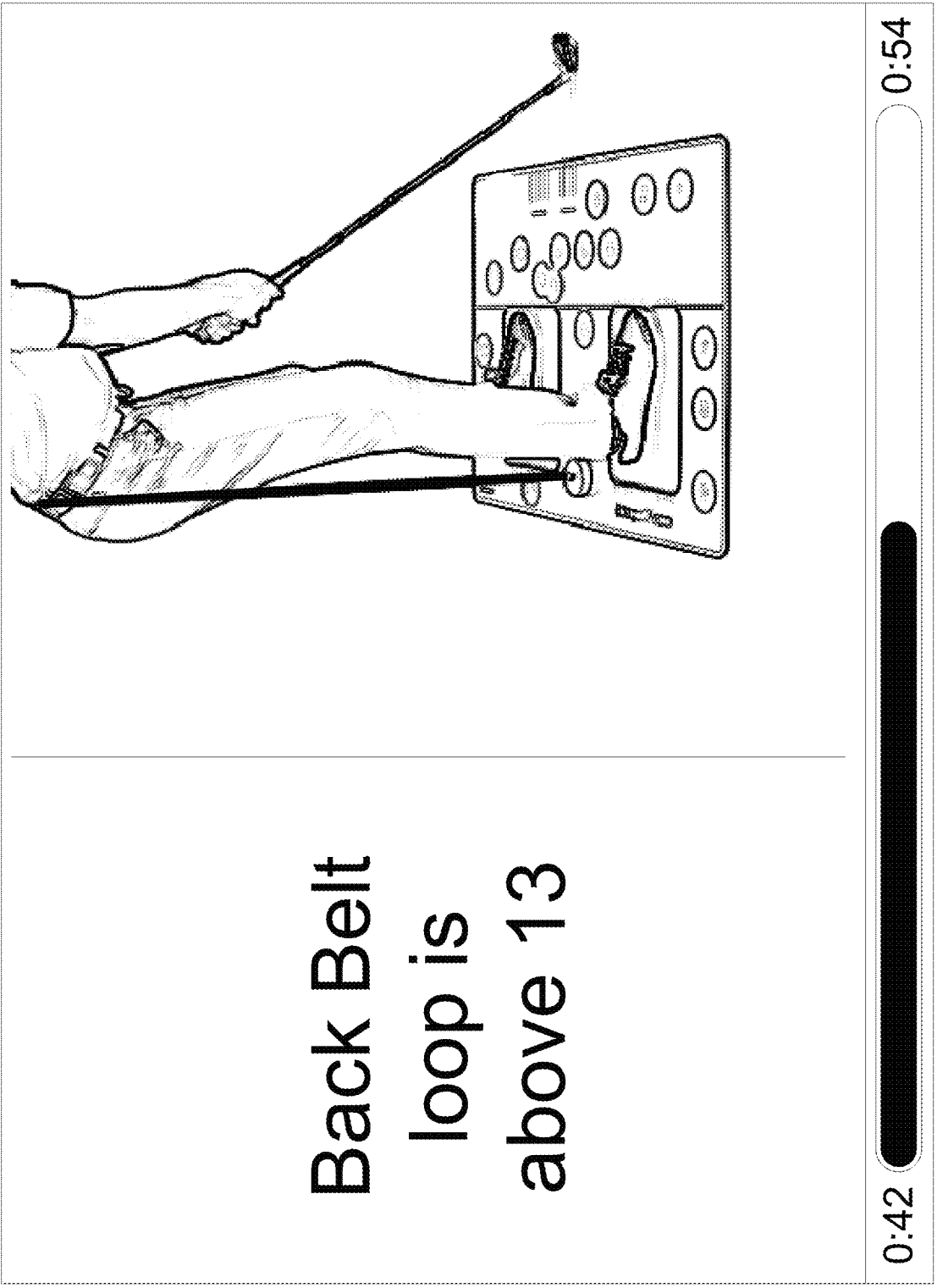
Figure 40:
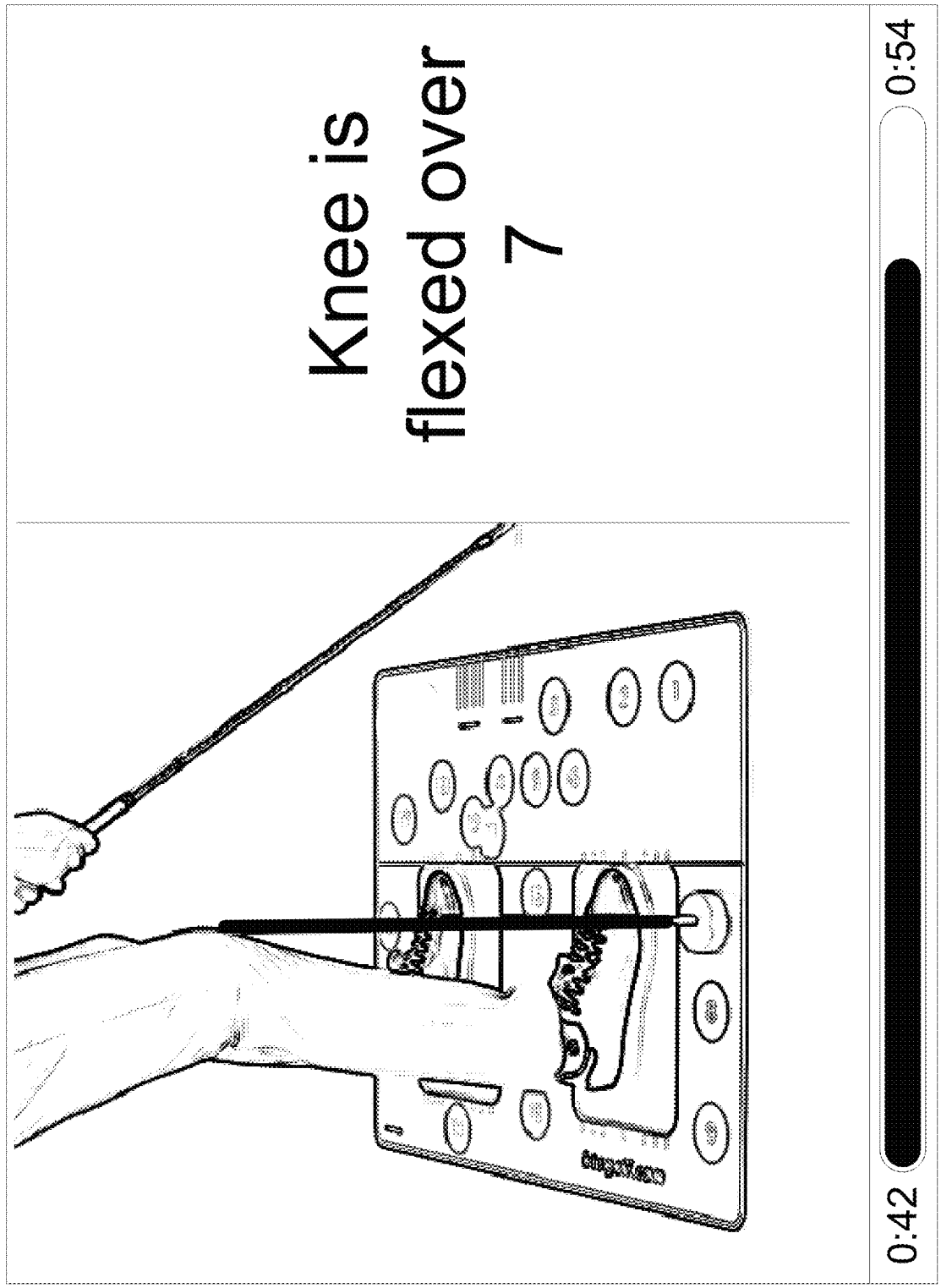

FIG. 30 is an illustration of an exemplary short peg component of an apparatus to be used with the body type specific information. The short peg includes a base 950 and a short stem 960S. It is substantially identical to the long peg of FIG. 29, except that the length of the stem is shortened such that the short peg is 6 in high. In alternative embodiments, bases of different diameters and stems of different heights than the examples shown can be used.

FIGS. 31-40 are illustrations of exemplary training guidance body type specific information provided using the exemplary method of FIG. 1, the exemplary system of FIG. 2, and the components of the apparatus of FIGS. 27-30. In this example, a 54 second clip is presented to the user to show them how to use the training carpet and pegs given their specific body type. At the step of FIG. 31, the general placement of the feet is shown to the user. At the step of FIG. 32, the user is instructed to place the left foot to align with the D indicia. At the step of FIG. 33, the user is instructed to place the right foot to align with the L indicia. At the step of FIG. 34, the user is instructed to place the long peg on the circular area numbered 16. At the step of FIG. 35, the user is instructed to place their belt buckle over the circular area numbered 16. Advantageously, the cooperation between the long peg, the body type specific information system, and the carpet enables this proper positioning. A highlighted line is provided in the info graphic to emphasize what the user should focus on. At the step of FIG. 36, the user is given guidance on how to position the angle of the left leg. Advantageously, the info graphic illustrates the angles by augmenting the picture of the golfer with highlight lines that show the correct positioning. At the step of FIG. 37, guidance is given to assist the user to position their hands ahead of the circular area numbered 16. Highlight circles are used to emphasize the position of the hands relative to the numbered circular area 16. At the step of FIG. 38, a profile view is presented to the user so that the user understands that their hands are ahead of the numbered area 16 in the profile as well as in the front view. A highlight circle and highlight line emphasize this in the info graphic. At the step of FIG. 39, the user is instructed to place their back belt loop above numbered circle 13, whereat is shown a peg and a highlight info graphic line. At the step of FIG. 40, the user is instructed to flex their knee over circle 7, whereat a left peg has been shown and a highlight line has been added to the info graphic. The above guidance was provided as an example only. It is contemplated by the inventor to decompose all guidance into reusable elements so that all 108 body type guidance can be provided using a minimal set of information resources. In alternative embodiments, the guidance is provided using augmented reality such that instead of an infographic, an overlay is provided in either 2D (e.g. on the ground) or 3D space (e.g. around the user and over an overlay of the training carpet or a real carpet).

Although not expressly shown, in alternative embodiments, it is contemplated that machine vision or motion capture can be utilised to derive all of the measurements required from the two images, the techniques required to do so being evident to those of skill in the relevant art.

Although not expressly shown in the drawings, in alternative embodiments of the user interface aspect that uses photographs to measure body type information, instead of using dots in the user interface to determine body type measurements from a photograph, lines, or a combination of dots and lines are used. In alternative embodiments of the carpet component, the carpet is provided as a virtual reality or augmented reality representation instead of a carpet. In alternative embodiments of the guidance information aspect, the guidance information is provided as a virtual reality or augmented reality presentation either over the real carpet or a virtual reality or augmented reality carpet.

One of the many advantages of providing access to guidance based on body type information is that the information provided is specific to the body type of the individual and therefore more pertinent to that individual, while at the same time guarding against use of that information from individuals who have different body types, thereby decreasing the likelihood that unauthorized copies of the body type specific information would be useable by others that are not authorized to access that information.

In alternative embodiments, the body type specific information is digitally watermarked or subject to digital rights management to further limit access to body type specific information to one or a group of authorized individuals only.

In alternative embodiments, body type measurements are obtained from a 3D model of the body of a golfer that is 3D scanned using a 3D scanner or motion sensing input device, or obtained from measurements made by a professional at a fitting session using a tape measure, or a combination of both.

Disclosed and illustrated herein are preferred embodiments. However, it is anticipated by the inventor that, for example, that the number of criteria, order of criteria, and range of criteria values may be configured differently to provide alternative embodiments of body type criteria, and that those criteria may be utilised to determine a body type that results in a different body type number, or that the body type may be represented using other information than a number. Therefore, any such variations are contemplated to be within the general scope of the present application. Likewise, variations on the apparatus components, information provided and body type specific information such as guidance are also contemplated to be within the scope of the present application.

Having described specific techniques of the aspects the application by way of example only, an environment in which specific techniques of the present application can operate will be further described by way of example only.

Figure 41:
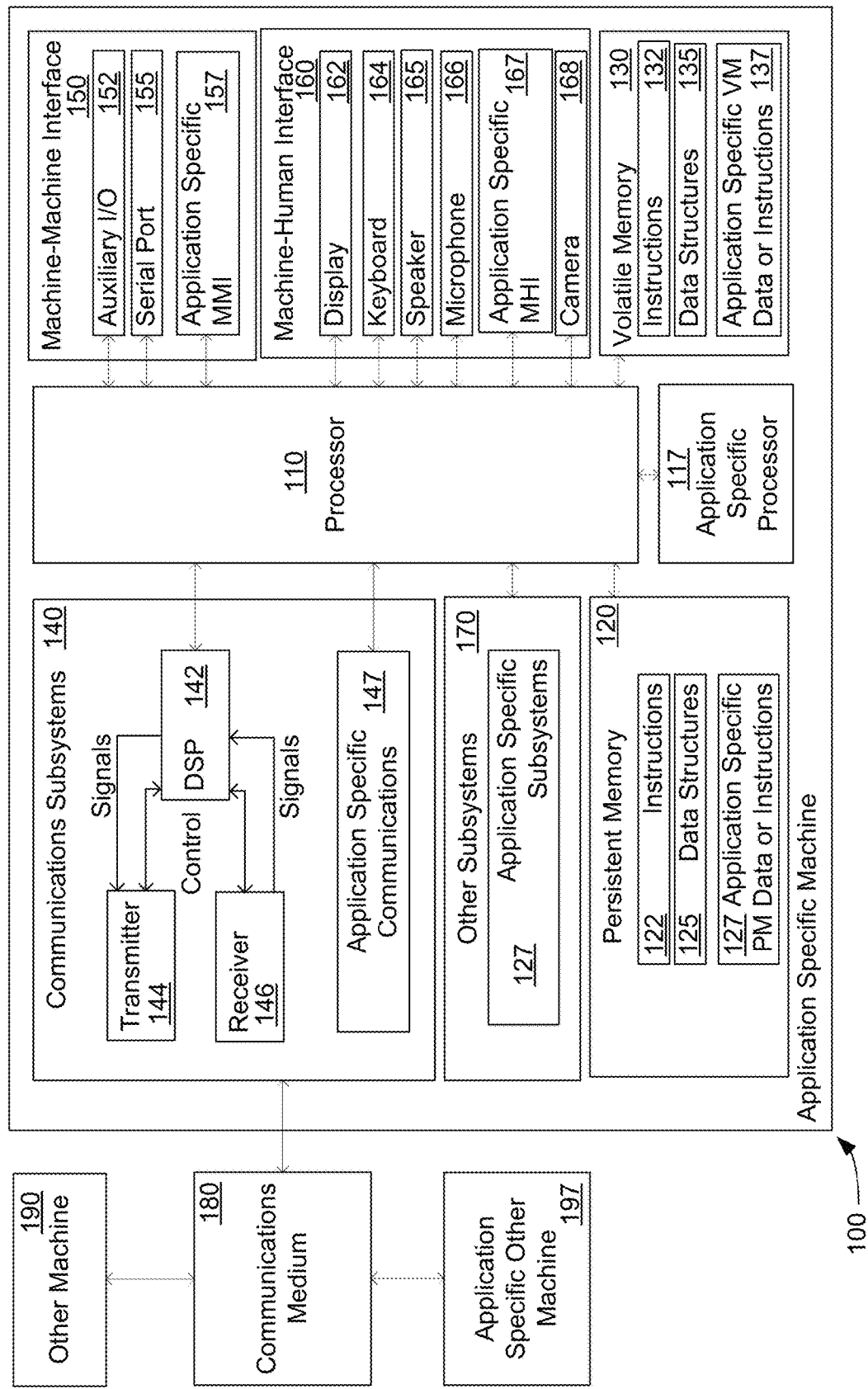
FIG. 41 is a block diagram of an exemplary application specific machine environment that can be used with embodiments of the present application.

FIG. 41 is a block diagram of an exemplary application specific machine environment that can be used with embodiments of the present application. Application Specific Machine 100 is preferably a two-way wireless or wired communication machine having at least data communication capabilities, as well as other capabilities, such as for example audio, and video capabilities. Application Specific Machine 100 preferably has the capability to communicate with other computer systems over a Communications Medium 180. Depending on the exact functionality provided, the machine may be referred to as a smart phone, a data communication machine, client, or server, as examples.

Where Application Specific Machine 100 is enabled for two-way communication, it will incorporate communication subsystem 140, including both a receiver 146 and a transmitter 144, as well as associated components such as one or more, preferably embedded or internal, antenna elements (not shown) if wireless communications are desired, and a processing module such as a digital signal processor (DSP) 142. As will be apparent to those skilled in the field of communications, the particular design of the communication subsystem 140 will be dependent upon the communications medium 180 in which the machine is intended to operate. For example, Application Specific Machine 100 may include communication subsystems 140 designed to operate within the 802.11 network, Bluetooth™ or LTE network, both those networks being examples of communications medium 180 including location services, such as GPS. Communications subsystems 140 not only ensures communications over communications medium 180, but also application specific communications 147. An application specific processor 117 may be provided, for example to process application specific data, instructions, and signals, such as for example for GPS, near field, or other application specific functions. Depending on the application, the application specific processor 117 may be provided by the DSP 142, by the communications subsystems 140, or by the processor 110, instead of by a separate unit.

Network access requirements will also vary depending upon the type of communications medium 180. For example, in some networks, Application Specific Machine 100 is registered on the network using a unique identification number associated with each machine. In other networks, however, network access is associated with a subscriber or user of Application Specific Machine 100. Some specific Application Specific Machine 100 therefore require other subsystems 127 in order to support communications subsystem 140, and some application specific Application Specific Machine 100 further require application specific subsystems 127. Local or non-network communication functions, as well as some functions (if any) such as configuration, may be available, but Application Specific Machine 100 will be unable to carry out any other functions involving communications over the communications medium 1180 unless it is provisioned. In the case of LTE, a SIM interface is normally provided and is similar to a card-slot into which a SIM card can be inserted and ejected like a persistent memory card, like an SD card. More generally, persistent Memory 120 can hold many key application specific persistent memory data or instructions 127, and other instructions x22 and data structures x25 such as identification, and subscriber related information. Although not expressly shown in the drawing, such instructions 122 and data structures 125 may be arranged in a class hierarchy so as to benefit from re-use whereby some instructions and data are at the class level of the hierarchy, and some instructions and data are at an object instance level of the hierarchy, as would be known to a person of ordinary skill in the art of object oriented programming and design.

When required network registration or activation procedures have been completed, Application Specific Machine 100 may send and receive communication signals over the communications medium 180. Signals received by receiver 146 through communications medium 180 may be subject to such common receiver functions as signal amplification, frequency down conversion, filtering, channel selection and the like, analog to digital (A/D) conversion. A/D conversion of a received signal allows more complex communication functions such as demodulation and decoding to be performed in the DSP 142. In a similar manner, signals to be transmitted are processed, including modulation and encoding for example, by DSP 142 and input to transmitter 144 for digital to analog conversion, frequency up conversion, filtering, amplification and transmission over the communication medium 180. DSP 142 not only processes communication signals, but also provides for receiver and transmitter control. For example, the gains applied to communication signals in receiver 146 and transmitter 144 may be adaptively controlled through automatic gain control algorithms implemented in DSP 144. In the example system shown in FIG. 41, application specific communications 147 are also provided. These include communication of information located in either persistent memory 120 or volatile memory 130, and in particular application specific PM Data or instructions 127 and application specific PM Data or instructions 137.

Communications medium 180 may further serve to communicate with multiple systems, including an other machine 190 and an application specific other machine 197, such as a server (not shown), GPS satellite (not shown) and other elements (not shown). For example, communications medium 180 may communicate with both cloud based systems and a web client based systems in order to accommodate various communications with various service levels. Other machine 190 and Application Specific Other machine 197 can be provided by another embodiment of Application Specific Machine 100, wherein the application specific portions are either configured to be specific to the application at the other machine 190 or the application specific other machine 197, as would be apparent by a person having ordinary skill in the art to which the other machine 190 and application specific other machine 197 pertains.

Application Specific Machine 100 preferably includes a processor 110 which controls the overall operation of the machine. Communication functions, including at least data communications, and where present, application specific communications 147, are performed through communication subsystem 140. Processor 110 also interacts with further machine subsystems such as the machine-human interface 160 including for example display 162, digitizer/buttons 164 (e.g. keyboard that can be provided with display 162 as a touch screen), speaker 165, microphone 166, one or more camera 168 (e.g. rear facing and/or front facing on a smartphone, or front facing only on a laptop or desktop computer), and Application specific HMI 167. Processor 110 also interacts with the machine-machine interface 1150 including for example auxiliary I/O 152, serial port 155 (such as a USB port, not shown), and application specific MHI 157. Processor 110 also interacts with persistent memory 120 (such as flash memory), volatile memory (such as random access memory (RAM)) 130. A short-range communications subsystem (not shown), and any other machine subsystems generally designated as Other subsystems 170, may be provided, including an application specific subsystem 127. In some embodiments, an application specific processor 117 is provided in order to process application specific data or instructions 127, 137, to communicate application specific communications 147, or to make use of application specific subsystems 127.

Some of the subsystems shown in FIG. 41 perform communication-related functions, whereas other subsystems may provide application specific or on-machine functions. Notably, some subsystems, such as digitizer/buttons 164 and display 162, for example, may be used for both communication-related functions, such as entering a text message for transmission over a communication network, and machine-resident functions such as application specific functions.

Operating system software used by the processor 110 is preferably stored in a persistent store such as persistent memory 120 (for example flash memory), which may instead be a read-only memory (ROM) or similar storage element (not shown). Those skilled in the art will appreciate that the operating system instructions 132 and data 135, application specific data or instructions 137, or parts thereof, may be temporarily loaded into a volatile 130 memory (such as RAM). Received or transmitted communication signals may also be stored in volatile memory 130 or persistent memory 120. Further, one or more unique identifiers (not shown) are also preferably stored in read-only memory, such as persistent memory 120.

As shown, persistent memory 120 can be segregated into different areas for both computer instructions 122 and application specific PM instructions 127 as well as program data storage 125 and application specific PM data 127. These different storage types indicate that each program can allocate a portion of persistent memory 120 for their own data storage requirements. Processor 110 and when present application specific processor 117, in addition to its operating system functions, preferably enables execution of software applications on the Application Specific Machine 100. A predetermined set of applications that control basic operations, including at least data communication applications for example, will normally be installed on Application Specific Machine 100 during manufacturing. A preferred software application may be a specific application embodying aspects of the present application. Naturally, one or more memory stores would be available on the Application Specific Machine 100 to facilitate storage of application specific data items. Such specific application would preferably have the ability to send and receive data items, via the communications medium 180. In a preferred embodiment, the application specific data items are seamlessly integrated, synchronized and updated, via the communications medium 180, with the machine 110 user's corresponding data items stored or associated with an other machine 190 or an application specific other machine 197. Further applications may also be loaded onto the Application Specific Machine 100 through the communications subsystems 140, the machine-machine interface 150, or any other suitable subsystem 170, and installed by a user in the volatile memory 130 or preferably in the persistent memory 120 for execution by the processor 110. Such flexibility in application installation increases the functionality of the machine and may provide enhanced on-machine functions, communication-related functions, or both. For example, secure communication applications may enable electronic commerce functions and other such financial transactions to be performed using the Application Specific Machine 100.

In a data communication mode, a received signal such as a text message or web page download will be processed by the communication subsystem 140 and input to the processor 110, which preferably further processes the received signal for output to the machine-human interface 160, or alternatively to a machine-machine interface 150. A user of Application Specific Machine 100 may also compose data items such as messages for example, using the machine-human interface 1160, which preferably includes a digitizer/buttons 164 that may be provided as on a touch screen, in conjunction with the display 162 and possibly a machine-machine interface 150. Such composed data items may then be transmitted over a communication network through the communication subsystem 110. Although not expressly show, the camera 168 can be re-used as both a machine-machine interface 150 by capturing coded images such as QR codes and barcodes, or reading and recognizing images by machine vision, as well as a human-machine interface 160 for capturing a picture of a scene or a user.

For audio/video communications, overall operation of Application Specific Machine 100 is similar, except that received signals would preferably be output to a speaker 134 and display 162, and signals for transmission would be generated by a microphone 136 and camera (not shown). Alternative voice or audio I/O subsystems, such as a voice message recording subsystem, may also be implemented on Application Specific Machine 100. Although voice or audio signal output is preferably accomplished primarily through the speaker 165, display 162 and applications specific MHI 167 may also be used to provide other related information.

Serial port 155 in FIG. 41 would normally be implemented in a smart phone-type machine as a USB port for which communication or charging functionality with a user's desktop computer, car, or charger (not shown), may be desirable. Such a port 155 would enable a user to set preferences through an external machine or software application and would extend the capabilities of Application Specific Machine 100 by providing for information or software downloads to Application Specific Machine 100 other than through a communications medium 180. The alternate path may for example be used to load an encryption key onto the machine through a direct and thus reliable and trusted connection to thereby enable secure machine communication.

Communications subsystems 140, may include a short-range communications subsystem (not shown), as a further optional component which may provide for communication between Application Specific Machine 100 and different systems or machines, which need not necessarily be similar machines. For example, the other subsystems 170 may include a low energy, near field, or other short-range associated circuits and components or a Bluetooth™ communication module to provide for communication with similarly enabled systems and machines.

The exemplary machine of FIG. 41 is meant to be illustrative and other machines with more or fewer features than the above could equally be used for the present application. For example, one or all of the components of FIG. 41 can be implemented using virtualization whereby a virtual Application Specific Machine 100, Communications medium 180, Other machine 190 or Application Specific Other Machine 197 is provided by a virtual machine. Software executed on these virtual machines is separated from the underlying hardware resources. The host machine is the actual machine on which the virtualization takes place, and the guest machine is the virtual machine. The terms host and guest differentiate between software that runs on the physical machine versus the virtual machine, respectively. The virtualization can be full virtualization wherein the instructions of the guest or virtual machine execute unmodified on the host or physical machine, partial virtualization wherein the virtual machine operates on shared hardware resources in an isolated manner, to hardware-assisted virtualization whereby hardware resources on the host machine are provided to optimize the performance of the virtual machine. Although not expressly shown in the drawing, a hypervisor program can be used to provide firmware for the guest or virtual machine on the host or physical machine. It will be thus apparent to a person having ordinary skill in the art that components of FIG. 41 can be implemented in either hardware or software, depending on the specific application. For example, while testing and developing the Application Specific Machine 100 may be provided entirely using an emulator for the machine, for example a smartphone emulator running Android™ or iOS™. When deployed, real smartphones would be used.

Each component in FIG. 41 can be implemented using any one of a number of cloud computing providers such as Microsoft's Azure™, Amazon's Web Service™, Google's Cloud Computing, or an OpenStack based provider, by way of example only. Thus, as will be apparent to a person having ordinary skill in the relevant field of art, depending on whether the environment in which operate the components of FIG. 41, the Communications medium 180 can be the Internet, an IP based medium such as a virtual, wired, or wireless network, an interconnect back plane on a host machine serving as a back bone between virtual machines and/or other real machines, or a combination thereof. For example, in the case of the communications subsystems 140, the Transmitter 144, Receiver 146 and DSP 142 may be unnecessary if the application specific machine is provided as a virtual machine. Likewise, when the application is a server provided as a virtual machine, the machine-human interface 160 and machine-machine interface 150 may be provided by re-use of the resources of the corresponding host machine, if needed at all.

The embodiments described herein are examples of structures, systems or methods having elements corresponding to elements of the techniques of this application. This written description may enable those skilled in the art to make and use embodiments having alternative elements that likewise correspond to the elements of the techniques of this application. The intended scope of the techniques of this application thus includes other structures, systems or methods that do not differ from the techniques of this application as described herein, and further includes other structures, systems or methods with insubstantial differences from the techniques of this application as described herein.

The above-described embodiments of the present techniques are intended to be examples only. Those of skill in the art may effect alterations, modifications and variations to the particular embodiments without departing from the scope of the techniques.

What is claimed is:

1. An apparatus for providing guidance information regarding a golf player's stance or swing as a function of the player's body type criteria, the apparatus comprising:
a body type criteria determination component to determine body type criteria;
a body type determination component to determine body type using the body type criteria;
a body type specific information selection component to select from a plurality of body type specific information using the body type; and
a rectangular carpet having a surface onto which are depicted:
(a) a plurality of feet indicia, for indicating pre-determined positions on the ground to place the golf player's feet relative to one another;
(b) a plurality of ball lines, for indicating pre-determined positions on the ground relative to the feet indicia, to place a golf ball relative to the ball lines; and
(c) a plurality of peg indicia, for indicating pre-determined positions on the ground relative to the feet indicia, for guiding the movements of the golf player's body, or the golf player's golf club, relative to the peg indicia;
wherein the pre-determined positions on the ground of the plurality of feet indicia, plurality of ball lines, and plurality of peg indicia account for a plurality of body types of golf players, such that, given the body type criteria of the golf player, the body type specific information is provided as a function of the golf player's body type referencing a select body type specific feet indicia, a select body type specific ball line, or a select body type specific peg indicia, the body type specific information including body type specific guidance to guide the stance or swing of the golf player as a function of the golf player's body type.

2. The apparatus of claim 1, wherein the rectangular carpet further comprises two rectangular areas to facilitate placement of the feet, a left foot rectangular area, and a right foot rectangular area, each rectangular area parallel with the other thereby delimiting the plurality of feet indicia such that each rectangular area has toe feet indicia at the top and heel feet indicia at the bottom for facilitating placement of the feet at the toe end and heel end, respectively.

3. The apparatus of claim 2, wherein the carpet is provided using a digital representation using one of a data structure, photograph, video, virtual reality, or augmented reality representation.

4. The apparatus of claim 1, further comprising at least one peg including a base parallel to the ground and a stem projecting upward from the base perpendicular to the ground, the peg suitable to be placed on at least one of the plurality of peg indicia.

5. The apparatus of claim 4, wherein the peg is provided with a hockey puck of 3 inches in diameter and the peg is 14 inches high or 6 inches high.

6. The apparatus of claim 4 wherein the peg is provided using a digital representation as one of a data structure, photograph, video, virtual reality, or augmented reality representation.

7. The apparatus of claim 1, wherein the body type criteria information includes arms length criteria, shoulder slant criteria, shoulder width criteria, hip width criteria, or shoulder projection information.

8. The apparatus of claim 1, wherein the arms length criteria includes short arms length (SA), average arms length (AA), or long arms length (LA).

9. The apparatus of claim 7, wherein the shoulder slant criteria includes low shoulder slant (SS02) or high shoulder slant (SS24).

10. The apparatus of claim 7, wherein the shoulder width criteria includes wide shoulders (WS), average shoulders (AS), or narrow shoulders (NS).

11. The apparatus of claim 7, wherein the hip width criteria includes narrow whips (NH), average hips (AH), or wide hips (WH).

12. The apparatus of claim 7, wherein the shoulder projection criteria includes low shoulder projection (SP02), or high shoulder projection (SP24).

13. The apparatus of claim 1, wherein the body type determination component includes a processor configured for determining at least one of:
(a) a height H;
(b) a neck to shoulder distance D(N,S);
(c) a waist size W;
(d) an elbow to belt distance D(E,B);
(e) a wrist to belt distance D(W,B);
(f) a hip width HW;
(g) a shoulder width SW; or
(h) a shoulder projection SP.

14. The apparatus of claim 13, wherein the processor is further configured to perform at least one of the following acts:
(a) authenticate a user;
(b) determine if a user is new;
(c) determine body information;
(d) store body information in a user profile;
(e) determine/store body type;
(f) lookup body type specific information; or
(g) provide body type specific information.

15. The apparatus of claim 14, wherein the determine body information act includes providing a user interface to receive body information from a user.

16. The apparatus of claim 14, wherein the user interface includes at least one prompt for a user height, a shoulder slant, a shoulder projection, a hip width, or a shoulder width.

17. The apparatus of claim 14, wherein the user interface includes at least one prompt for a front facing photograph of the user, a side stance photograph of the user, or a height.

18. The apparatus of claim 1, wherein the body type specific information includes pictures, videos, infographics, basic setup guidance, basics guidance, takeaway/backswing/impact guidance, finish guidance, or body type specific guidance.

19. The apparatus of claim 1, wherein the body type specific information references at least one of the plurality of feet indicia, plurality of ball lines, plurality of peg indicia of the apparatus of claim 1.

\* \* \* \* \*